US010379051B2

(12) United States Patent
Imai et al.

(10) Patent No.: US 10,379,051 B2
(45) Date of Patent: Aug. 13, 2019

(54) ILLUMINATION DEVICE AND BIO-INFORMATION MEASUREMENT DEVICE HAVING THE SAME

(71) Applicant: KABUSHIKI KAISHA TOSHIBA, Minato-ku, Tokyo (JP)

(72) Inventors: Kaita Imai, Tokyo (JP); Shouhei Kousai, Yokohama Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 257 days.

(21) Appl. No.: 15/068,486

(22) Filed: Mar. 11, 2016

(65) Prior Publication Data
US 2017/0074797 A1    Mar. 16, 2017

(30) Foreign Application Priority Data

Sep. 14, 2015  (JP) ................... 2015-181202

(51) Int. Cl.
*B01L 3/00* (2006.01)
*C12M 3/00* (2006.01)
(Continued)

(52) U.S. Cl.
CPC ..... *G01N 21/6486* (2013.01); *G01N 21/6456* (2013.01); *G01N 27/028* (2013.01); *G01N 33/4833* (2013.01)

(58) Field of Classification Search
CPC ..... B01L 2300/0636; B01L 2300/0645; B01L 3/502715; G01N 21/6486; G01N 27/028; G01N 21/6456
See application file for complete search history.

(56) References Cited

U.S. PATENT DOCUMENTS

| 6,856,161 B2 | 2/2005 | Thewes |
| 7,737,088 B1 | 6/2010 | Stahler et al. |

(Continued)

FOREIGN PATENT DOCUMENTS

| JP | 2002523781 A | 7/2002 |
| JP | 2006284225 A | 10/2006 |

(Continued)

OTHER PUBLICATIONS

Japanese Office Action dated Aug. 30, 2016, issued in counterpart Japanese Application No. 2015-181202.
(Continued)

*Primary Examiner* — Nathan A Bowers
(74) *Attorney, Agent, or Firm* — Holtz, Holtz & Volek PC

(57) ABSTRACT

According to one embodiment, the illumination device includes a lighting unit and a control unit. The lighting unit emits light at the intensity to be emitted toward the region to be irradiated in a two-dimensional region of a measurement device. The measurement device acquires optical information and biochemical information and/or electrical information for an object corresponding with positional information. The control unit determines the region to be irradiated and the intensity to be emitted, based on the biochemical or electrical information by the measurement device, the positional information of them, and the threshold conditions predetermined, and controls the irradiation of the lighting unit depending on them.

10 Claims, 19 Drawing Sheets

(51) Int. Cl.
*G01N 21/64* (2006.01)
*G01N 27/02* (2006.01)
*G01N 33/483* (2006.01)

(56) References Cited

U.S. PATENT DOCUMENTS

| | | | |
|---|---|---|---|
| 2004/0040868 A1* | 3/2004 | DeNuzzio | B01L 3/5085 205/792 |
| 2006/0160164 A1 | 7/2006 | Miller et al. | |
| 2009/0026082 A1* | 1/2009 | Rothberg | C12Q 1/6869 204/556 |
| 2009/0205201 A1* | 8/2009 | Xu | C12M 23/12 29/825 |
| 2010/0233698 A1* | 9/2010 | Joseph | B01L 3/50851 435/6.14 |
| 2011/0300569 A1* | 12/2011 | Li | G01N 33/4836 435/29 |
| 2013/0258076 A1 | 10/2013 | Fujimoto et al. | |
| 2013/0331295 A1 | 12/2013 | Ahn et al. | |
| 2014/0262783 A1* | 9/2014 | Chang | G01N 27/44721 204/452 |
| 2015/0027885 A1* | 1/2015 | Rajaraman | G01N 33/4836 204/403.13 |
| 2015/0376692 A1* | 12/2015 | Esfandyarpour | C12Q 1/6874 506/2 |
| 2017/0038282 A1* | 2/2017 | Veiseh | G01N 1/10 |

FOREIGN PATENT DOCUMENTS

| | | |
|---|---|---|
| JP | 2007505319 A | 3/2007 |
| JP | 4133028 B2 | 8/2008 |
| JP | 5077799 B2 | 11/2012 |
| JP | 2013228361 A | 11/2013 |
| WO | 2016104517 A1 | 6/2016 |

OTHER PUBLICATIONS

Guoan Zheng, et al., "The ePetri dish, an on-chip cell imaging platform based on subpixel perspective sweeping microscopy (SPSM)", vol. 108, No. 41, Oct. 11, 2011, 9 Pages.

Kannie W. Y. Chan, et al., "MRI-detectable pH nanosensors incorporated into hydrogels for in vivo sensing of transplanted-cell viability", Nature Materials, vol. 12, Mar. 2013, pp. 268-275.

Xiwei Huang, et al., "A 64×64 1200fps CMOS Ion-Image Sensor with Suppressed Fixed-Pattern-Noise for Accurate High-throughput DNA Sequencing", 2014 Symposium on VLSI Circuits Digest of Technical Papers, Jun. 10-13, 2014, pp. 134 and 135.

\* cited by examiner

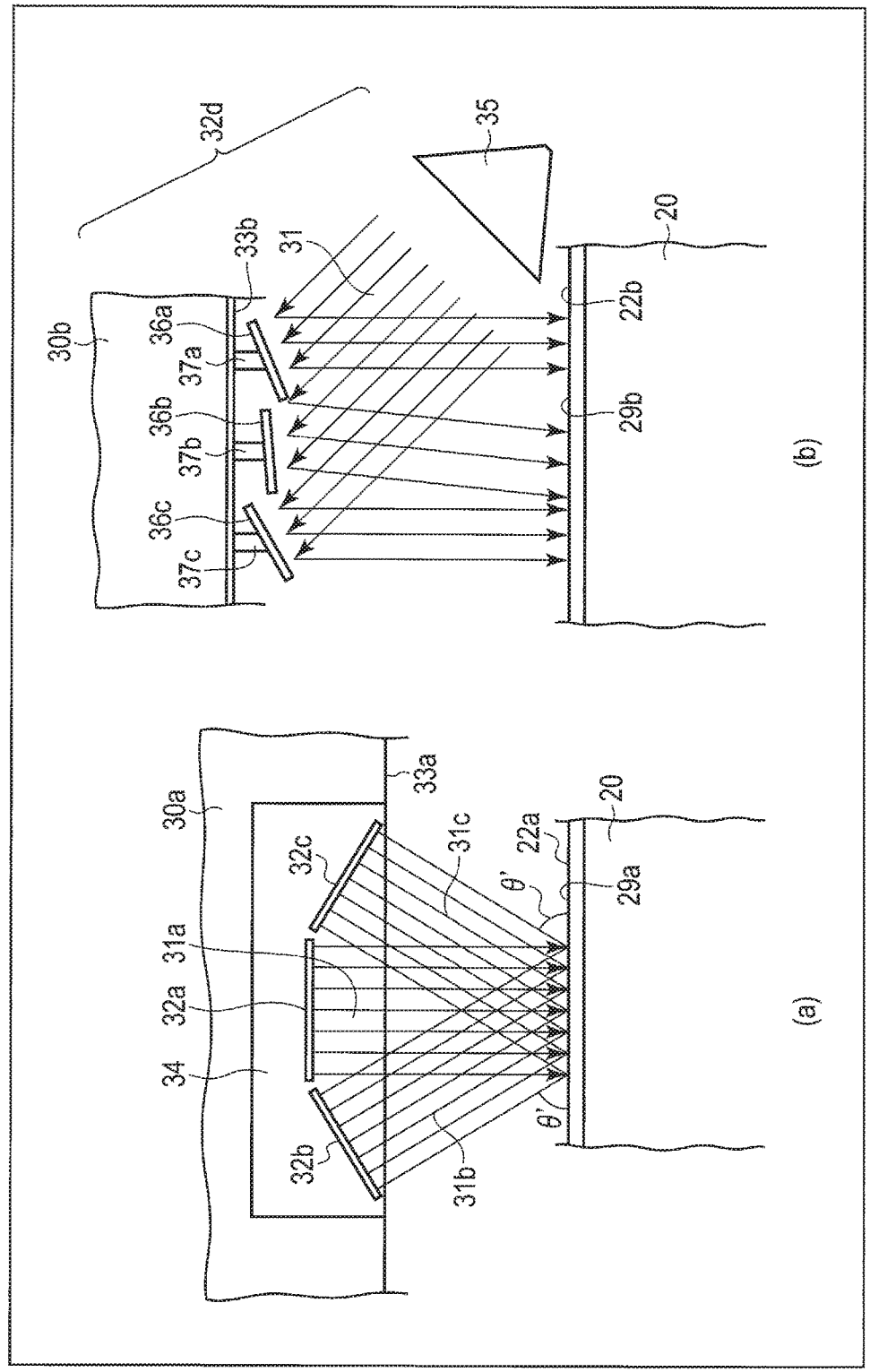
F I G. 3

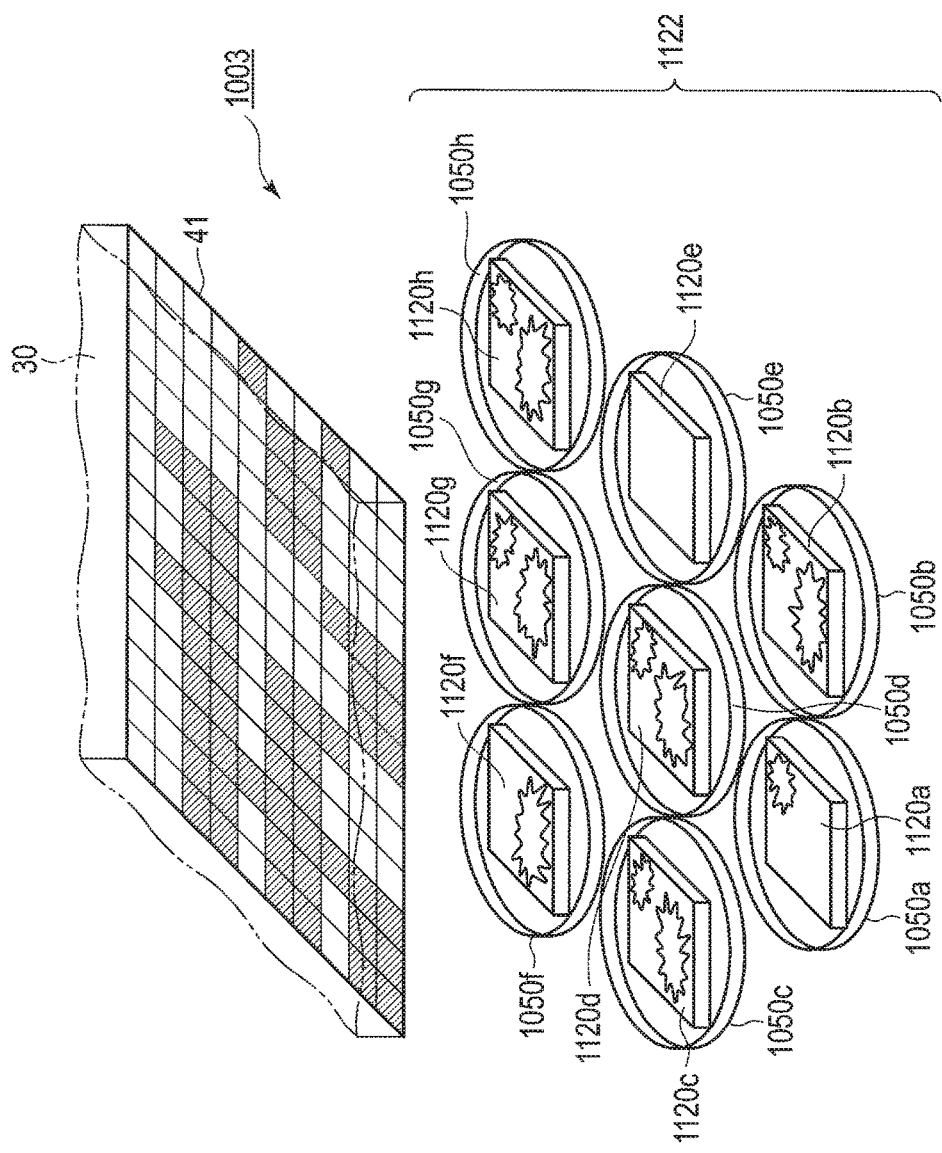
F I G. 12

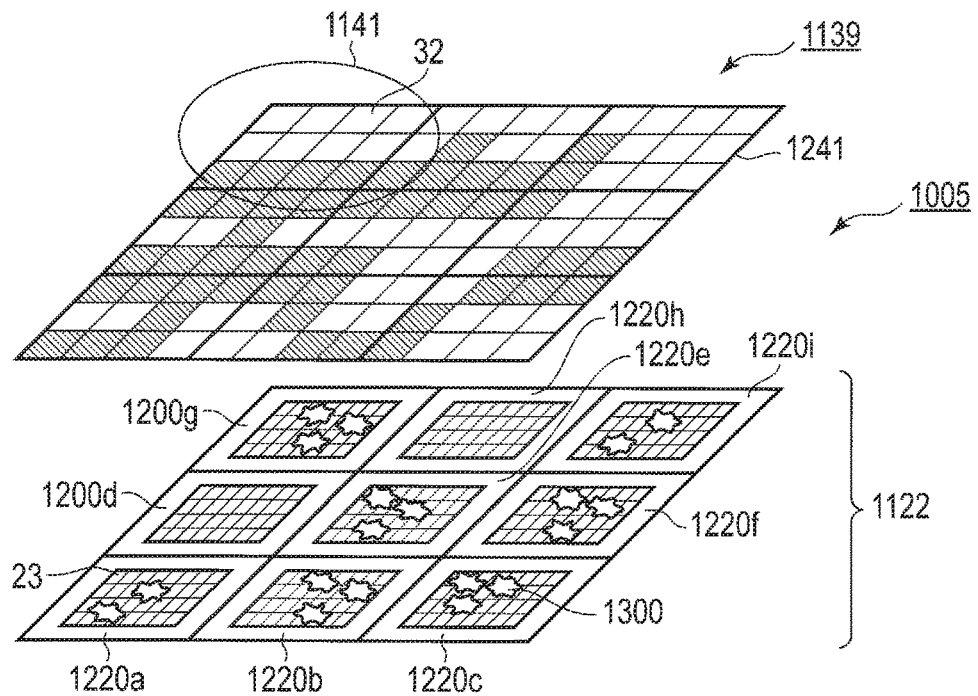
F I G. 14
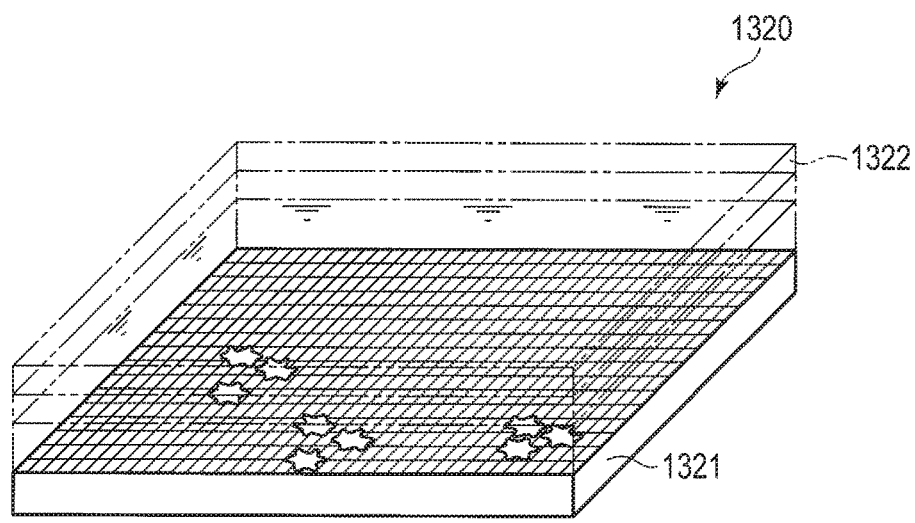
F I G. 15

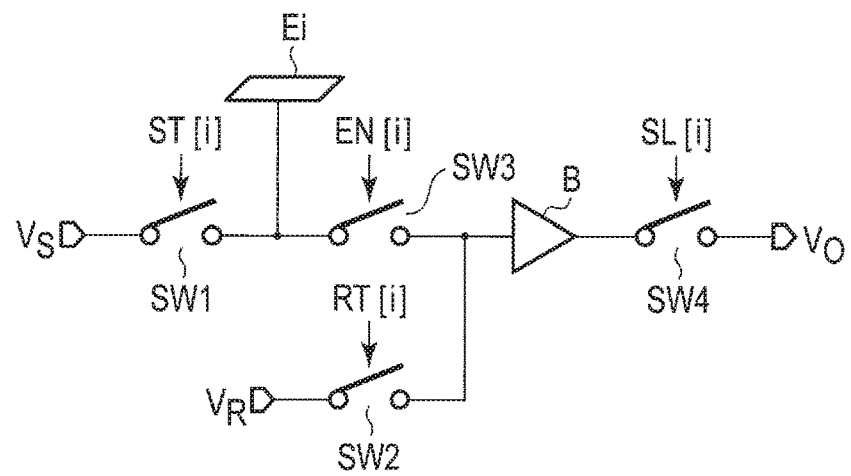
F I G. 22
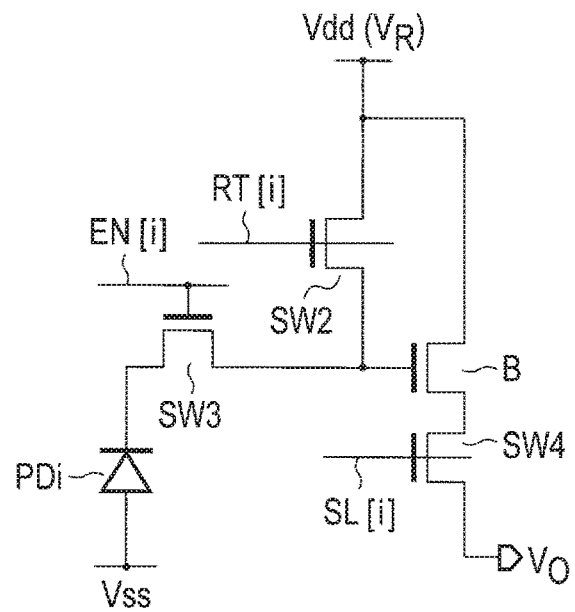
F I G. 23

ILLUMINATION DEVICE AND BIO-INFORMATION MEASUREMENT DEVICE HAVING THE SAME

CROSS-REFERENCE TO RELATED APPLICATIONS

This application is based upon and claims the benefit of priority from Japanese Patent Application No. 2015-181202, filed Sep. 14, 2015, the entire contents of which are incorporated herein by reference.

FIELD

Embodiments described herein relate generally to an illumination device and a bio-information measurement device including the same.

BACKGROUND

In order to achieve a social system that enables people to live healthily and comfortably, studies to reveal causes of diseases and pathogenic mechanisms of the diseases and studies related to preventing or curing methods based on the above studies have been performed. There has been suggested a process for reducing the risk of developing diseases by collecting and analyzing information on the diseases revealed by the studies and information such as pathogenic factors in individuals (e.g., congenital, postnatal, and lifestyle factors).

Meanwhile, various types of measurement devices for performing bio-measurement on a semiconductor chip are developed. Examples of the measurement device include a measurement device that measures an ion concentration, a measurement device that measures light, a measurement device that observes the chemical behavior of a test substance based on the fluorescence intensity measurement, and a measurement device that observes the activity of cells based on the electrical potential measurement.

In the meanwhile, several illumination devices for measurement device are suggested. An example of such illumination devices is an illumination device for using the measurement device, which acquires a pH and an optical image. It also suggests that a personal digital assistant display uses as the illumination device for the measurement device.

BRIEF DESCRIPTION OF THE DRAWINGS

FIG. 3 is a pattern diagram showing examples of lighting unit groups according to the embodiment;

FIG. 12 is an image view showing an example of a sensor matrix or a lighting unit matrix array, which correspondingly includes in the bio-information measurement device according to the embodiment;

FIG. 14 is an image view showing an example of a sensor matrix array or a lighting unit matrix array, which correspondingly includes in the bio-information measurement device according to the embodiment;

FIG. 15 is a perspective diagram showing an example of the measurement device according to the embodiment;

FIG. 22 is a circuit diagram showing an example of each subblock of the measurement device according to the embodiment; and FIG. 23 is a circuit diagram showing an example of each subblock of the measurement device according to the embodiment.

DETAILED DESCRIPTION

In general, according to one embodiment, the illumination device includes a lighting unit and a control unit.

The lighting unit emits light at the light intensity to be emitted toward the region to be irradiated in a two-dimensional region of a measurement device. The measurement device acquires optical information and biochemical information and/or electrical information for a test sample presented on the two-dimensional region, corresponding to positional information of the test sample on the two-dimensional region. The control unit determines the region to be irradiated in the two-dimensional region and the light intensity to be emitted, based on the biochemical information or the electrical information obtained by the measurement device, the positional information mapped with the information, and the threshold conditions predetermined corresponding to the information, and controls the light irradiation of the lighting unit depending on the determined region and intensity.

Hereinafter, various embodiments will describe with reference to the drawings. The drawings are schematic and not shown at an accurate scale.

Figure 1:
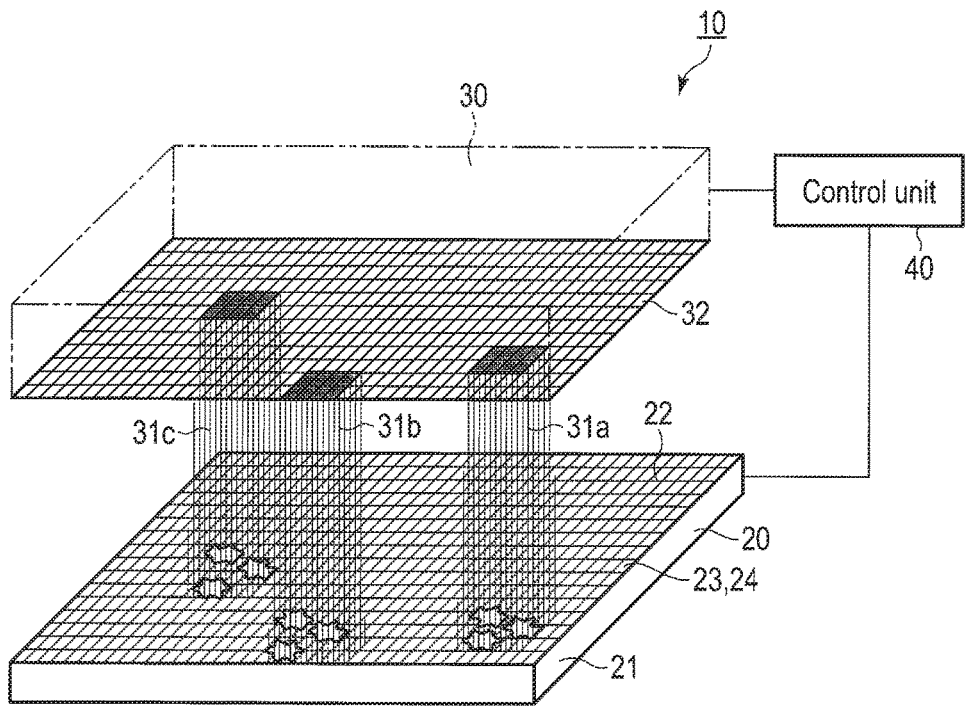
FIG. 1 is a schematic perspective diagram showing an example of a bio-information measurement device according to an embodiment.

As shown in FIG. 1, a bio-information measurement device 10 according to the embodiment includes a measurement device 20, an illumination device 30 that emits light at a specific light intensity, and a control unit 40 that controls the light irradiation to the illumination device 30. The illumination device 30 irradiates a specific region in a sensor matrix included in the measurement device 20 with light. The measurement device 20, the illumination device 30, and the control unit 40 electrically connect with each other.

Examples of sensing by the measurement device 20 include sensing of light information, sensing of chemical substance information, and sensing of electric information. Here, the sensing of light information performs by receiving the light emitted from the illumination device 30, which is disposed facing the sensing region of the measurement device 20. According to the device of the embodiment, irradiation is performed under control of the control unit 40 based on the results obtained by the sensing of chemical substance information and/or the sensing of electric information by the measurement device 20. The irradiation conditions include the light irradiation region by the illumination device 30, light intensity, and light irradiation time and timing. The light irradiation more appropriately controls under such conditions. Accordingly, the bio-information measurement device 10 according to the embodiment can measure a test sample more economically and efficiently, compared to the device in the past.

The bio-information measurement device 10 operates, for example, as follows. (1) The light irradiation by the illumination device turns off. (2) The sensing of chemical substance information and/or the sensing of electric information performs to measure a cell signal. (3) The illumination range determines taking into consideration the spatial resolution of the illumination device, the spatial resolution of the measurement device, and diffusion of light. (4) The illumination device emits light to only the pixel region obtained the cell signal. (5) A moving image acquires by repeating the steps (1) to (4); and (6) the light intensity appropriately controls for each irradiation region.

When cultured cells are substances measured in the bio-information measurement device 10, for example, cells isolated from the living body are seeded on the sensor matrix including in the measurement device 20 and then the device 10 is placed in an incubator for cultivation. The bio-information measurement device 10 measures predefined items of the cells under the culture condition. At the early stage of cultivation, a small number of the cells are present on the sensor matrix. According to the embodiment, it is possible to determine the region where the cells are present based on the information obtained by the sensing of chemical substance information and/or the sensing of electric information. In the device in the past, observation performs after irradiation of the whole sensor matrix with light. Therefore, the light irradiation by the illumination device 30 can be limited, for example, only to a specified region, which is more economical.

On the other hand, a biological sample in a normal or disease state may influence to a greater or a lesser extent by exposure to light stimulation. Therefore, in some cases, it is preferable to minimally suppressing the irradiation of the test sample with light. According to the bio-information measurement device 10 of the embodiment, it is possible to select the light irradiation conditions or the presence or absence of light irradiation, for example, corresponding to the conditions of cells. For example, when the cells as the test samples become apoptotic or necrotic, or are weakened, it is requested that the light irradiation is minimized. In that case, an indicator suggesting apoptosis, necrosis or weakness (e.g., an indicator such as a pH or a cell metabolite) performs on the test sample prior to the light irradiation. Then, it is possible to select the light irradiation conditions or the presence or absence of light irradiation. Thus, measurement data can obtain effectively.

Unpredefined light irradiation can prevent, thereby making it possible to obtain a more accurate result. In such a case, the threshold conditions used to determine the light irradiation conditions or the presence or absence of light irradiation may be any indicator to indicate specific conditions of the test sample. The threshold conditions may include a threshold defined in advance and a pattern defined in advance. For example, a threshold determination process or a determination process using pattern matching, machine learning, and statistical processing uses to determine the light irradiation conditions or the presence or absence of light irradiation. However, the conditions are not limited thereto. The threshold conditions are, for example, conditions including a threshold for determining whether the light irradiation performs or does not. An example of threshold conditions is as follows: "when the pH is lower than a specific value, the light irradiation performs"; or "when the pH is higher than a specific value, the light irradiation does not perform (or the light is turned off)".

Hereinafter, the bio-information measurement device 10 will describe more in detail.

[Measurement Device]

The measurement device 20 includes a substrate 21, and a sensor matrix 22 presents on the surface of the substrate 21. The sensor matrix 22 is an array including a plurality of sensor pixels 23, i.e., a sensor pixel array. A sensor pixel 23 configures to include a basic block. In the sensor matrix 22, a predefined number of basic blocks having the same configuration align to a matrix.

The signal detected by the measurement device 20 may be a cell/cells signal from a test sample. The "information to be detected" may include light information, ion information, electric information, temperature, other information, and the like. Examples of the light information include light intensity, fluorescence intensity, bioluminescence intensity, phosphorescence intensity, and autofluorescence intensity. Examples of the electric information include potential, current, voltage, and impedance. Such information may include time-dependent changes in predefined items. The type of the sensor element selects depending on the information detected.

A basic block includes at least two types of sensor elements 24 depending on the information detected. One of the types is a photosensor element. The photo-sensor element acquires light information on the test sample sensed. The light information is information on any light obtained by irradiating the test sample with light. The photo-sensor element may be a semiconductor element that senses a light signal and converts the signal in an electric signal. The light sensed may be visible light, ultraviolet light, infrared light, fluorescence, phosphorescence, luminescence or the like. Thus, it is possible to obtain morphological information on the test sample, distribution of the test sample, and information on the distribution, concentration, and behavior of a substance mapped with the test sample. Examples of the photo-sensor element include a CMOS image sensor which converts the light detected by a photodiode into an electric signal, a SPAD image sensor which converts the light detected by a single-photon avalanche diode (SPAD) into an electric signal, an image sensor used a solid-state image sensing device such as a CCD image sensor, and a sensor used a thermoelectric conversion element such as a thermopile sensor.

The sensor element except the photo-sensor element including the basic block may be a chemical sensor element and/or an electric sensor element.

The chemical sensor element may be a semiconductor element that senses a characteristic of a chemical substance or its change and converts it into an electric signal. Thus, the chemical sensor element detects physical, chemical, and biochemical changes in the chemical substance. The chemical sensor element may be a semiconductor sensor element. The semiconductor sensor element can sense an ion such as $H^+$, $K^+$ or $Ca^{2+}$, a neurotransmitter such as acetylcholine, a metabolic product formed extracellularly or intracellularly, a metabolite such as a substance metabolized, a specific antigen or antibody, or a protein derived therefrom. The semiconductor sensor element converts a signal based on information from the chemical substance detected into an electric signal. Examples of the chemical sensor element include ion sensitive or chemical field-effect transistors, ISFETs, and CHEMFETs.

The electric sensor element is a semiconductor element that acquires electric information on the test sample. The electric sensor element may be a semiconductor element. The semiconductor element senses a potential, a current, a voltage or impedance in order to detect potential information such as action potential of cells, the adhesion and contact between a cell and the device 20, the adhesion and contact between cells, and the activation and activated state of test samples such as cells. The electric sensor element may produce a current or voltage signal. Further, the sensor element may be a temperature sensor element. The sensing of each of the elements and the conversion of the information obtained by the sensing into an electric signal may perform under control of a control system. Furthermore, a sensor element for detecting other substances may be included. Examples of the electric sensor element include a semiconductor sensor that is used an electrode and a semiconductor voltage sensor.

In the sensor matrix 22 according to the embodiment, at least one type of sensor element (except for the type of the photosensor element) selects from and includes in the basic block in combination with the photosensor element.

The sensor elements including the basic block form a matrix with a predefined number thereof. A sensor element including in the basic block provides a sub pixel. In other words, the sensor pixels 23 forming the sensor matrix 22 provide by the basic block. The sensor pixels 23 configure to include a plurality of sub pixels.

The sensor element includes a sensing unit which is faced the front side of the measurement device 20 (not shown). A sub pixel provides by a sensor element and corresponds to the sensing unit of the sensor element. The sensing unit corresponds to a sub pixel. The sensor pixels 23 include a plurality of sub pixels. In a sensor pixel 23, a predefined number of the sub pixels form a submatrix.

Figure 2:
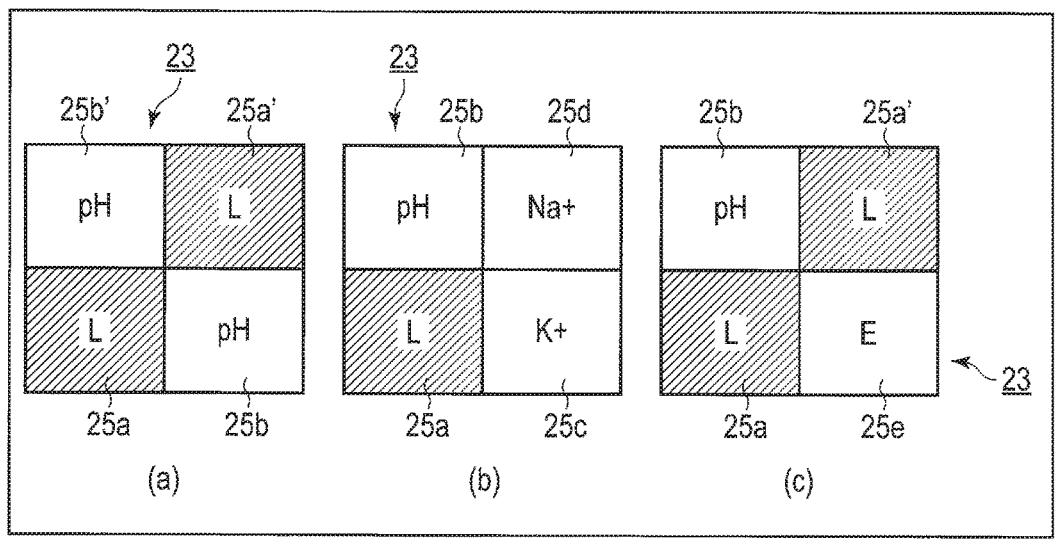
FIG. 2 is a diagram showing examples of sub pixel matrices of the measurement device according to the embodiment.

Examples of the sensor pixels 23 are shown in (a), (b) and (c) of FIG. 2. Each of the sensor pixels 23 shown in (a) to (c) of FIG. 2 includes four sub pixels in which two rows and two columns arrange in a matrix. Each of the four sub pixels is the sensing unit of the sensor element. Four sensing units shown in FIG. 2 (a) are a first optical sensing unit 25a, a second optical sensing unit 25a', a first pH sensing unit 25b, and a second pH sensing unit 25b', respectively. In the sensing units 25a, 25a', 25b, and 25b', different types of the sensing units are disposed adjacent to one another. In other words, one side of the first optical sensing unit 25a contacts with a side of the first pH sensing unit 25b. The other side of the first pH sensing unit 25b contacts with one side of the second optical sensing unit 25a'. The other side of the first optical sensing unit 25a contacts with the other side of the second pH sensing unit 25b'. Further, the other side of the second pH sensing unit 25b' contacts with the other side of the first optical sensing unit 25a.

The size of each of the sensor pixels may be, for example, in a range of from 300 nm×300 nm to 20 μm×20 μm, in a range of from 300 nm×300 nm to 10 μm×10 μm or in a range of from 300 nm×300 nm to 1 μm×1 μm, respectively. The size may change depending on the type of sensor element. In the case of the other pixels, the size of pixels may be determined, for example, depending on the amplitude of the signal sensed. The pitch between the sensor pixels may be, for example, from 0.3 μm to 30 μm. However, it is not limited thereto.

In the example of FIG. 2 (b), the sensor pixel 23 includes an optical sensing unit 25a, a pH sensing unit 25b, a potassium ion sensing unit 25c, and a sodium ion sensing unit 25d. In the sensor pixel 23, one side of a sensing unit is adjacent to each of the sensing units of detection elements of different types.

In the sensor pixel 23 shown in FIG. 2 (c) as an example, all the sensing units including in the sensor pixel 23 detect different information or items.

According to an embodiment, the sensor matrix 22 including a plurality of the basic blocks as a sensor pixel 23 forms a surface of the measurement device 20, and acquires the bio-information on test samples present on the surface (e.g., cells cultured on the sensor matrix 22) as a two-dimensional image.

Thus, the sensing unit of the sensor element provides a sub sensor pixel 25, and the basic block formed of a plurality of sub sensor pixels 25 provides a sensor pixel 23. A predefined number of the sensor pixels 23 arrange in a matrix to form a sensor pixel array. Hence, the sensor matrix 22 is an assembly of a predefined number of the sensor pixels forming a matrix.

The measurement device 20 acquires optical information and biochemical information and/or electrical information for the test sample present on a two-dimensional region provided by the sensor matrix 22, corresponding with the positional information on the two-dimensional region. A two-dimensional image may create from the obtained information. The image produced from the light signal, which obtains by the photosensor element, may use as an alternative for the image taken with a microscope.

[Illumination Device]

FIG. 1 shows that the illumination device 30 emits specific lights 31a, 31b, and 31c to specific regions on the sensor matrix 22 of the measurement device 20. The lights 31a, 31b, and 31c selectively emit to three regions where the cells are present on the sensor matrix 22. The illumination device 30 shown in this example includes a plurality of lighting units 32 on the surface which is faced the sensor matrix 22. A predefined number of the lighting units 32 arrange in a matrix on a surface of the illumination device 30, which is faced the sensor matrix 22. These lighting units 32 form a lighting unit array. The number of the lighting units 32 is the same as, smaller than, or larger than the number of the sensor pixels 23 including the sensor matrix 22, which selectively emit the lights to the specific regions on the sensor matrix 22. The size of the sensor pixel 23 and the size of the lighting unit 32 are the same as or different from each other.

The lighting position adjustment of the illumination device 30 with the sensor matrix 22 is performed. The light having a specific light intensity emit to a specific region of the sensor matrix 22 from the illumination device 30 under control of the control unit 40.

The lighting unit 32 may be, for example, an organic EL, an LED or a laser. A predefined number of the lighting units may form a matrix. Examples thereof include an organic EL display, a liquid crystal display, a laser, a laser array, an LED array, and a laser scanner. The organic EL display, LED array or laser scanner may include at least one of the lighting units. An illumination of the measurement device 20 by the illumination device 30 may be surface light emission, point light emission or linear light emission. For example, in the case of point light emission or linear light emission, in the case of the illumination device 30 including a plurality of lighting units, or in the case of a single lighting unit, the position of the lighting unit and/or the measurement device may move. The lighting unit and/or the measurement device emit a light in order to scan a two-dimensional region provided by the lighting unit from one end to the other end.

When the illumination device includes a plurality of lighting units, the lighting units may emit lights having different wavelengths. In order to emit different wavelengths, the illumination device may include a filter in a light emitting unit of a lighting unit. The light emitted to one region includes visible lights such as red light, green light, blue light, and white light; ultraviolet light; infrared light; a combination of two or more lights selected from these lights; and a combination of lights having not only a specific light color but also a specific wavelength or lights having a plurality of different wavelengths. The light may select as predefined.

An angle in which the light emitted from the lighting unit enters into the optical sensing unit (i.e., an incident angle) may select as predefined. For example, the light emitted from the lighting unit may vertically enter into the optical sensing unit, or may enter obliquely to the optical sensing unit.

FIG. 3 (a) and FIG. 3 (b) show examples in which the light emitted from the lighting unit irradiates obliquely to the optical sensing unit 29b. FIG. 3 (a) is an example of a lighting unit group to emit three lights having different wavelengths to a region. In this example, the lighting unit group includes a first lighting unit 32a that emits a first specific wavelength, a second lighting unit 32b that emits a second specific wavelength, and a third lighting unit 32c that emits a third specific wavelength, respectively. The lighting unit group is disposed in a recess 34 formed on a surface 33a which is faced a predefined region of the sensor matrix 22a of the illumination device 30a. The first lighting unit 32a is disposed parallel to and immediately above the optical sensing unit 29a in the corresponding position. The light emitted from the first lighting unit 32a emits light vertically to the optical sensing unit 29a located immediately below the lighting unit. The light emitted from the second lighting unit 32b irradiates obliquely (i.e., at an incident angle θ of less than 90°) into the optical sensing unit 29a. Similarly, the light emitted from the third lighting unit 32c irradiates obliquely (i.e., at an incident angle θ of less than 90°) into the optical sensing unit 29a. When the light emits from the first lighting unit 32a, the light controls not to emit from the second lighting unit 32b and the third lighting unit 32c. In other words, when any light emits from any of the first lighting unit 32a, the second lighting unit 32b, and the third lighting unit 32c, light may not emit from the rest of the lighting units. The corresponding optical sensing unit 29a may include a filter for allowing the wavelength to be detected to be selectively incident. In the case of using in combination with the filter, an incident angle θ of less than 90° is advantageous because of the selection of the wavelength by the filter.

An example of the optical lighting unit is shown in FIG. 3 (b). The optical lighting unit 32d includes a light source 35 located below the illumination device 30b, mirrors 36a, 36b, and 36c (collectively referred to as a mirror 36), and a mirror angle changing mechanism 37 which changes or adjusts the angle to the sensor matrix 22b of the mirror 36 as predefined. The mirror 36 changes an optical path by reflecting the light emitted from the light source 35 and emits light to a predefined region of the sensor matrix 22b. For example, the mirror 36 is a digital mirror device (DMD). The optical lighting unit 32d during use emits light from the light source 35, and reflects the emitted light by the mirror 36 fixed on the surface 33b which is faced the sensor matrix 22b of the illumination device 30b so as to direct the light to a predefined region of the sensor matrix 22b. Thus, the light emits to a specific region of the sensor matrix 22b, and made incident at a predefined angle onto the optical sensing unit 29b present in the region

[Control Unit]

The control unit 40 controls the bio-information measurement device 10. The measurement device 20 acquires optical information and biochemical information and/or electrical information for the test sample on a two-dimensional region, corresponding to the positional information on the two-dimensional region. The control unit 40 determines the presence or absence of illumination from the illumination device 30 or the illumination conditions based on the information from the measurement device 20.

Figure 4:
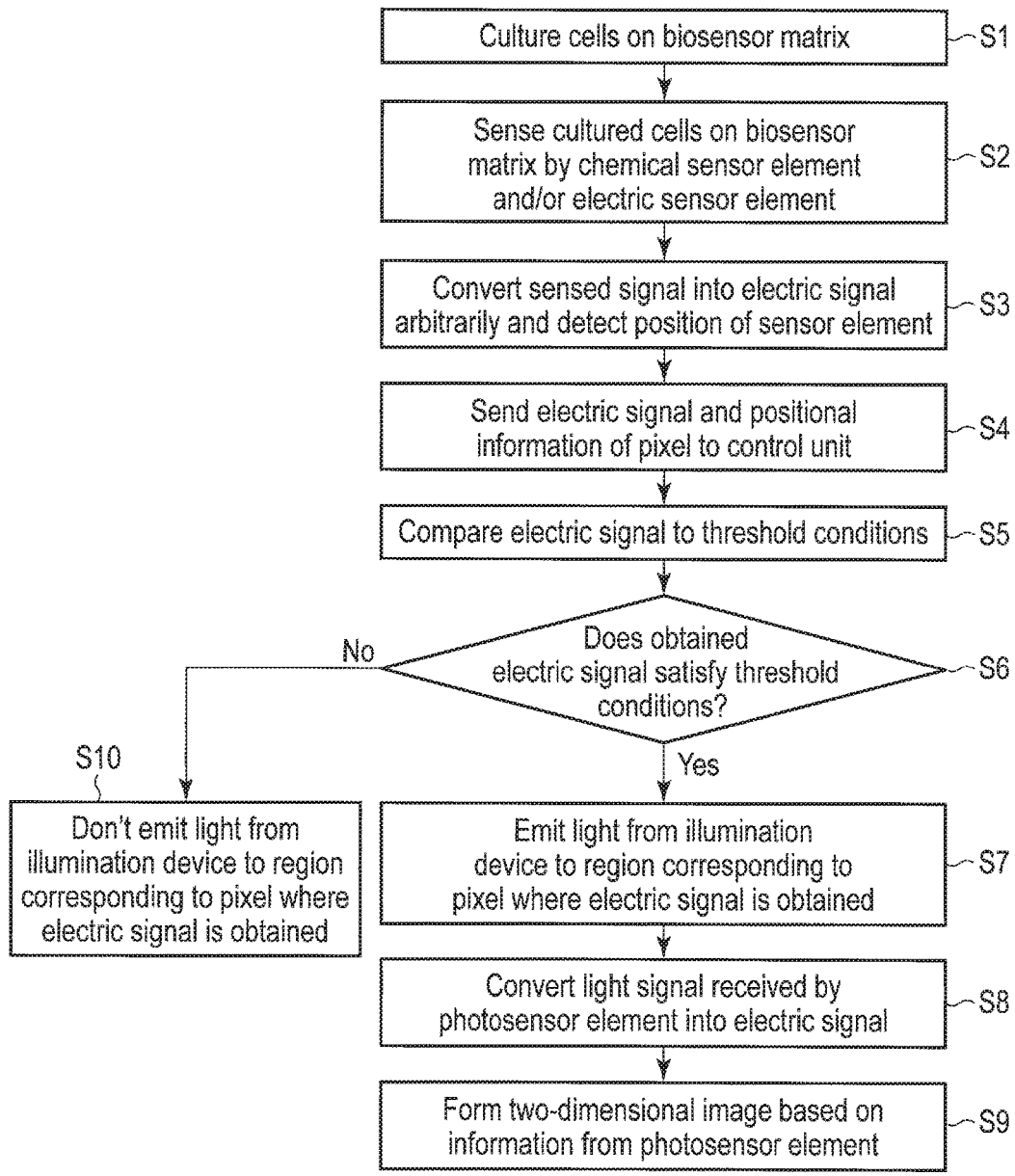
FIG. 4 is a flow chart showing an example of a measurement procedure in the bio-information measurement device according to the embodiment.

An example of measurement using the bio-information measurement device 10 performed under control of the control unit 40 will describe with reference to FIG. 4. First, an operator seeds test samples (e.g., cells) onto the sensor matrix 22 of the measurement device 20 placed in a culture dish and cultures them in an incubator (S1). At this time, the illumination device 30 is disposed in a state of aligning at the corresponding position. Subsequently, the sensor element 24 acquires information on the cells in a state of placing in the incubator under control of the control unit 40 according to the program stored in advance (S2). At this time, light irradiation of the illumination device 30 is still in an off state. Under control of the control unit 40, the sensor element 24 converts the obtained result into an electric signal and sends the signal to the control unit 40, or does not convert the signal sensed as an electric signal and sends the signal to the control unit 40. The control unit 40 receives the signal and detects the position of a sensor pixel on the sensor matrix (S4). The sensor pixel includes the sensor element 24, the sensor element 24 having obtained the electric signal. The control unit 40 compares the received electric signal to the threshold conditions determined in advance (S5). Then, the control unit 40 determines whether the provided electric signal satisfies the threshold conditions based on the comparison result (S6). The control unit 40 repeats a processing loop of steps S2 to S6 to form a two-dimensional image. From a result of the determination of S6 under control of the control unit 40, the Illumination device 30 emits light to a region and a region under the illumination conditions allocated to the threshold conditions (S7). The former region locates in the sensor matrix 22 corresponded to the position of the sensor pixel 23 which satisfies the threshold conditions. The latter region locates in a specific range predetermined. The sensor element 24 detects the light emitted from the illumination device 30 under control of the control unit 40, converts the obtained light signal into an electric signal, and sends the signal to the control unit 40 (S8). The control unit 40 forms a two-dimensional image from all the signals received from the sensor element 24 (S9). In the case where an electric signal does not satisfy the threshold conditions, light irradiation from the illumination device does not perform on the region corresponding to the pixel obtained the electric signal (S10). In such measurement, according to the operator's decision, light irradiates the entire surface or a part of the sensor matrix at arbitrary timing, and the interrupt control may perform to obtain a two-dimensional image.

The information on the test sample detected or measured based on the threshold conditions may be, for example, the determination of the presence or absence of cells (or state of the presence of cells), the determination of the cell state, the determination of environment around cells or the like. A decision regarding the presence or absence of cells determines whether the cells are present on the sensor pixel. An indicator for determining the presence or absence of cells may be, for example, a potential, a pH, an ion concentration, a neurotransmitter or a cell metabolite.

For example, the decision for the cell state may determine in accordance with the cell strain as the test sample, the experiment objective, and the type of reagent added or introduced to the test sample. For example, it knows that the intracellular pH changes when comparing dead and weakened cells to normal cells. Therefore, it is possible to determine such a cell state using a pH as an indicator.

For example, it is possible to examine the active state and function of cells by detecting intracellular and extracellular ion concentrations or pericellular ion concentration, cell metabolites or the like. Therefore, it is possible to determine the cell state based on the detected signals regarding the above items. For example, as for the degree of the adhesion between cells, impedance can use as its indicator. As a result, the organized state of the cells can be determined. For example, as for the formation of the network of nerve cells, an action potential can use as an indicator. Such information may be information itself, or may be a component or item constituted the threshold conditions. The threshold conditions are information for determining the conditions of illumination from the illumination device.

The size of information (single or complex information) serving as an indicator, time-dependent changes, relative characteristics, pattern, and specific item's threshold are used as threshold conditions. When these threshold conditions reach a specific value or state, the illumination region to be selected, the light intensity, the illumination time, the illumination interval, and the presence or absence of light irradiation are predetermined as the illumination conditions. The information obtained by corresponding the threshold conditions with the illumination conditions is previously stored in the control unit. The mapped information to be stored may be in any form such as a table or a list.

Control of each device, control over a plurality of devices or control of the whole bio-information measurement device based on the control unit may perform in accordance with the program previously stored in the control unit or the table obtained by corresponding the conditions with the operation.

For example, a process of obtaining information on the presence or absence of cells using a pH as an indicator may include the following step of acquiring a pH image. The indicator is based on being higher or lower than the pH of a cell culture medium or the average of the whole measurement region. For example, "the presence of cells" when the pH is high, "the absence of cells" when the pH is low or the other way around is predetermined as the threshold conditions. For example, in the case where the detected pH is higher than the threshold, "the presence of cells" is determined, to set such that irradiated light performs to the sensor pixel obtained the signal with a specific light intensity, and arbitrarily to the periphery of the sensor pixel. The range of the periphery of the sensor pixel may predetermine by a practitioner as predefined.

Figure 5:
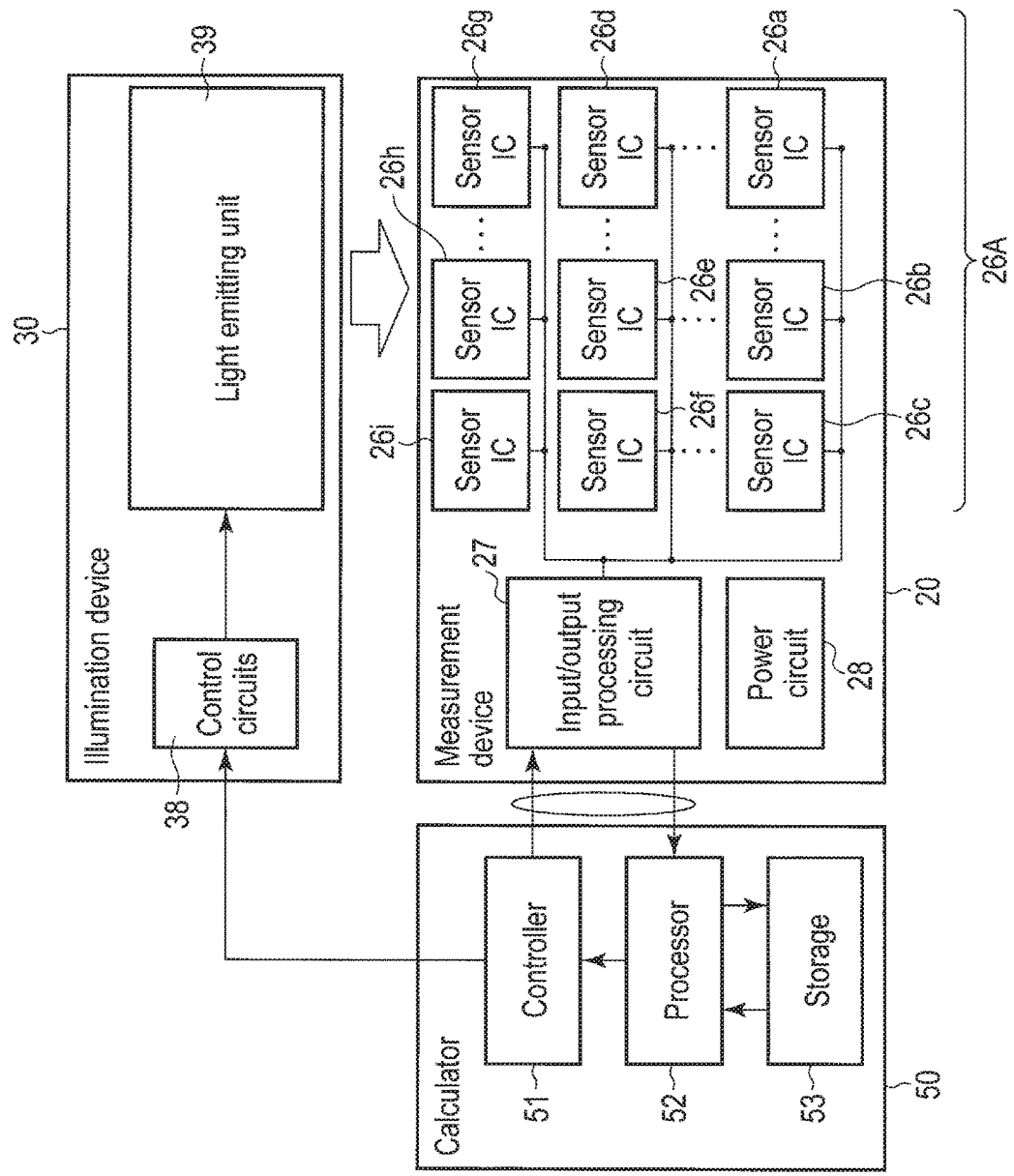
FIG. 5 is a block diagram showing a configuration of the bio-information measurement device according to the embodiment.

For example, the bio-information measurement device 10 according to the embodiment may control by the control system described below. An example of the control system will describe with reference to FIG. 5.

The measurement device 20 includes a plurality of sensor ICs 26 comprising a sensor element (namely, sensor ICs 26a to 26i collectively refer to as "sensor IC 26"). A predefined number of these sensor ICs form a matrix. The sensor IC 26 electrically connects to an input/output processing circuit sent and received signals. The measurement device 20 includes a power circuit 28. The circuit 28 electrically connects so that an electric power supplies to all the configurations of the bio-information measurement device 10.

The input/output processing circuit 27 includes in the measurement device 20 and electrically connected to the sensor IC 26 and a controller 51 and a processor 52 in a control device 50. The input/output processing circuit 27 performs input/output processing of a signal among the sensor IC and the units. The control device (calculator) 50 includes the controller 51, the processor 52, and a storage device 53. These units electrically connect to one another directly or indirectly.

If necessary, the information obtained by each of the sensor elements converts into an electric signal and sends to the processor 52 through the sensor IC 26 and the input/output processing circuit 27.

The storage device 53 previously stores a program for allowing the controller 51 totally to control the bio-information measurement device 10 and a program for controlling each configuration. Further, the storage device 53 stores the information to associate or map the threshold conditions with the illumination conditions as data such as a table or a list. If necessary, the storage device 53 may further store a program, a table or the like. Measurement by the measurement device and/or light irradiation by the illumination device may perform temporally, intermittently or continuously. Further, the storage device 53 may store all the measuring results and the corresponding positional information.

The processor 52 performs data processing such as calculation and produces a two-dimensional image based on the data, program, and table stored in the storage device 53 under control of the controller 51. Based on the cell state during the last measurement and data stored in the storage device 53 as well as the illumination conditions at that time, the processor 52 may change the illumination conditions and newly produce illumination conditions.

The controller 51 electrically connects to a control circuit 38 of the illumination device 30. The control circuit 38 electrically connects to a light emitting unit 39, and controls the presence or absence of illumination, light intensity, illumination region, illumination interval, illumination time, light-emitting wavelength, and incident angle of the light emitted from the light emitting unit 39, in accordance with the illumination conditions. The control performed by the control circuit 38 may control by the control device 50.

The light emitting unit 39 includes a plurality of lighting units (not shown). Each of the lighting units is disposed so as to correspond to each of the positions of the basic blocks (i.e., sensor pixels) including in the measurement device 20. Alternatively, a lighting unit allocates to a plurality of adjacent basic blocks. The allocation of the lighting unit to the basic blocks may perform as predefined. The ratio between the lighting unit and the basic blocks, which are corresponded to each other, may be, for example, any of 1×1:1×1 to 1×1:10×10, 1×1:1×1 to 1×1:100×100, 1×1:1×1 to 1×1:1000×1000 and 1×1:1×1 to 1×1:1000 or more ×1000 or more.

In the above example, the measurement device 20 includes a plurality of sensor ICs 26. In this regard, all or some of sensor elements and basic blocks in the sensor matrix may control by a sensor IC 26.

The control unit may be a calculator such as a computer. In the above example, the calculator includes the controller, the processor, and the storage device. In this regard, in addition to these components, the calculator may include an input unit, an image processing unit, an output unit, and a radio wave sending/receiving unit.

The control device 50, the illumination device 30, and the measurement device 20 electrically connect to one another. The devices may connect by a cable or radio.

Figure 6:
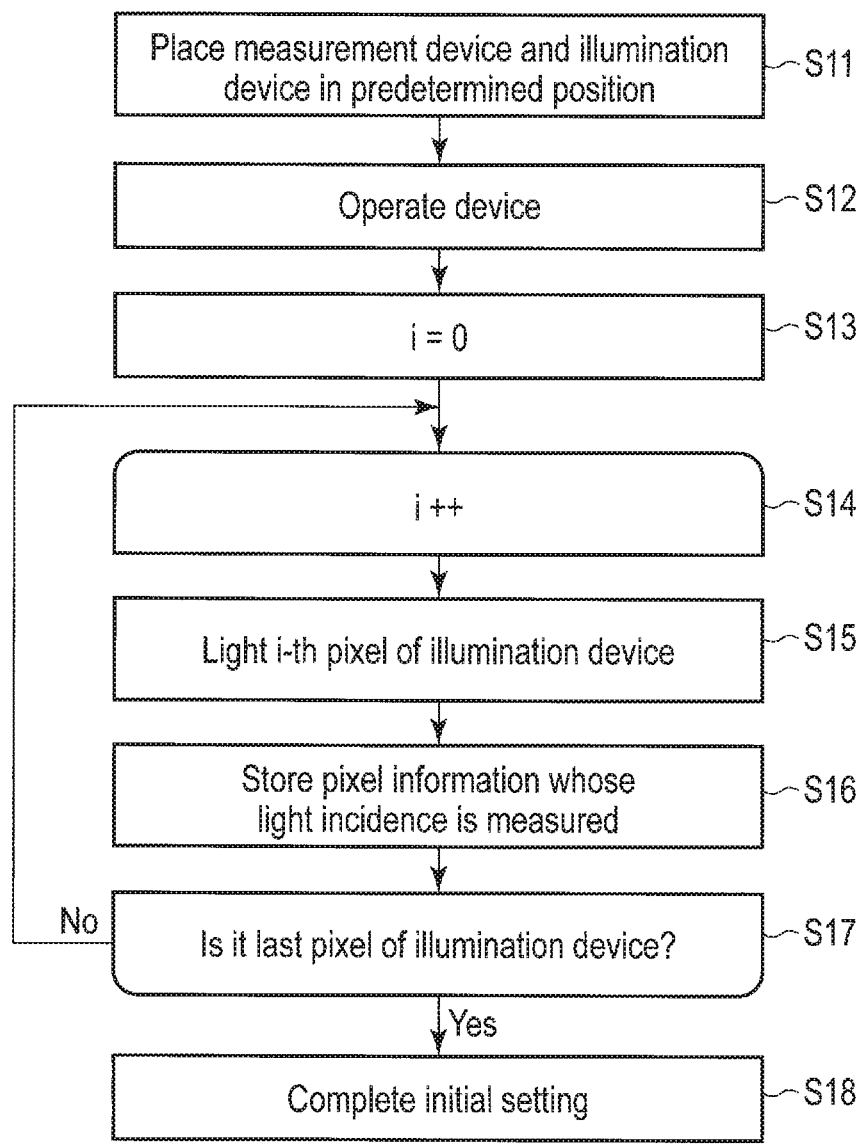
FIG. 6 is a flow chart showing an example of an alignment correction procedure of the bio-information measurement device according to the embodiment.
Figure 7:
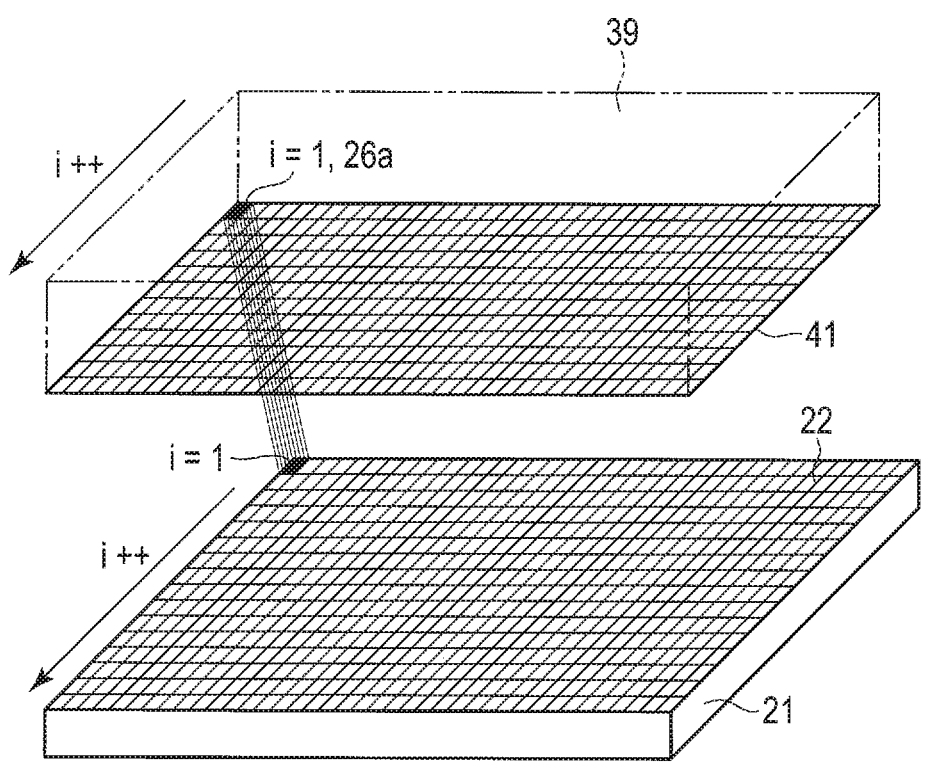
FIG. 7 is an image view showing a part of an example of a measurement device or an illumination device with which the alignment correction according to the embodiment conducts.
Figure 8:
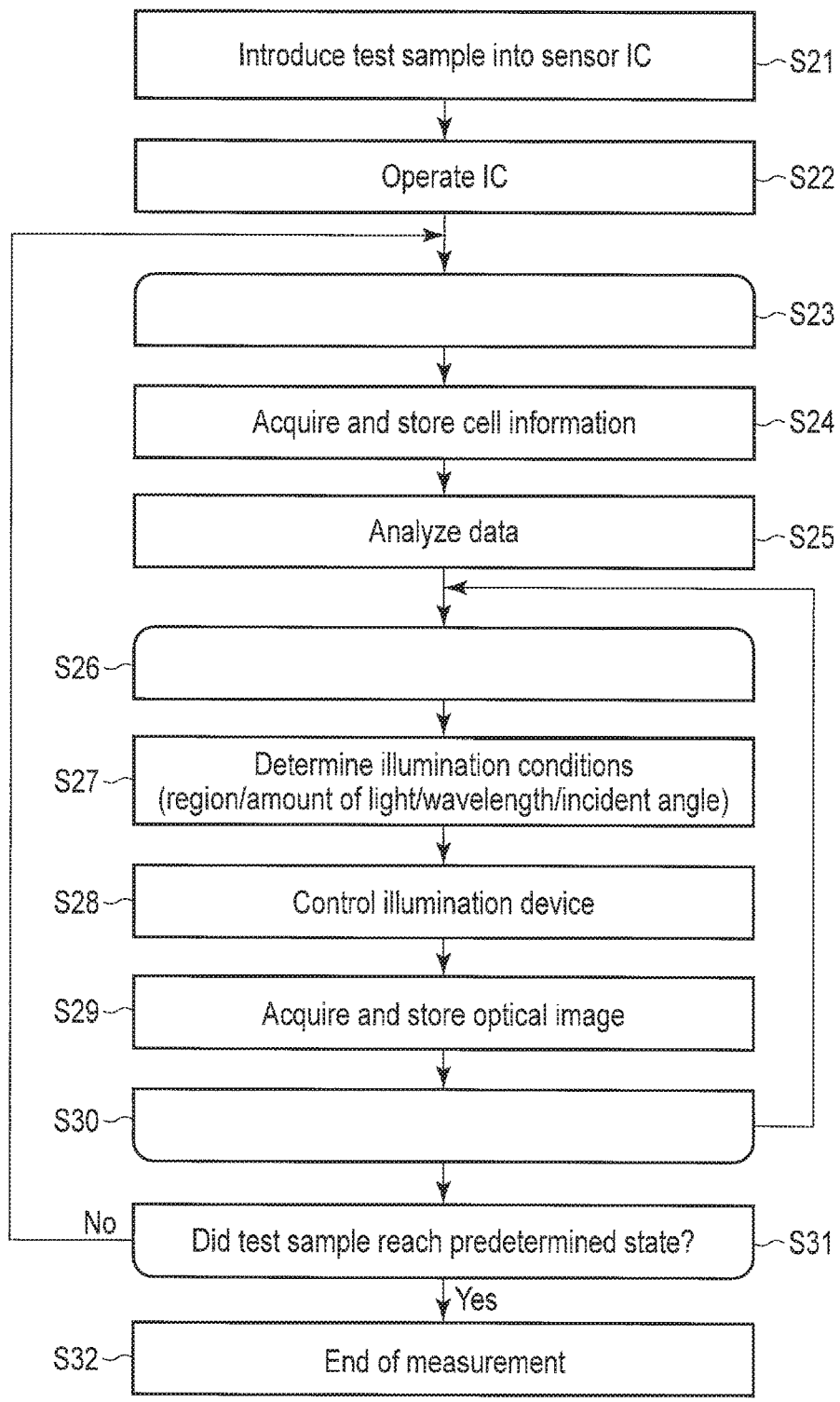
FIG. 8 is a flow chart showing an example of a procedure for executing the measurement by the bio-information measurement device according to the embodiment.

An operation procedure related to the measurement by the bio-information measurement device 10 will describe with reference to FIGS. 6 to 8.

FIG. 6 is a flow chart showing an example of alignment correction between the measurement device 20 and the illumination device 30 which is performed in an initial setting of the device. FIG. 7 is an example of the object on which the process shown in FIG. 6 performs and is a pattern diagram where parts of the measurement device and the illumination device respectively draw out and shown. FIG. 8 is a flow chart of the operation of measurement performed by the bio-information measurement device 10.

Subsequently, the alignment correction between the measurement device 20 and the illumination device 30, which performs in an initial setting of the device, will describe.

First, the operator places the measurement device 20 and the illumination device 30, which position so as to face each other, in a dark room (S11). The operator gives an instruction to start the operation from an input unit (not shown). The controller 51 receives the instruction and actuates the bio-information measurement device 10 to start an alignment correction process (S12). In the initial setting, i sets to 0 (S13). The controller 51 counts up i (S14). The light emitting unit 39 lights a first sensor pixel in the sensor matrix 22 (light incidence) (S15), and simultaneously records that this sensor pixel is the first sensor pixel (i.e., i=1) in the sensor matrix 22 (not shown). The processor 52 receives light information as a signal amplified by the sensor IC, pixel information (i.e., a position of the pixel which has detected the incident light) or the like from the input/output processing circuit 27, and maps the light information with the positional information, and stores the resulting information in the storage device 53 (S16). The processor 52 determines whether an i-th pixel is or not the last pixel present in the sensor matrix 22 (S17). When the processor 52 determines the sensor pixel is not the last pixel, the process proceeds to S14. Then, the steps S14 to S17 repeat until the processor 52 determines that pixel information on the last pixel present in the sensor matrix 22 obtained. When the processor 52 determines that pixel information on the last pixel present in the sensor matrix 22 obtains, the process proceeds to S18 and the alignment correction process is finished.

The alignment correction process may automatically perform immediately after the starting-up of the bio-information measurement device 10 in the initial setting. Once the alignment correction process performs, initialization processing is not necessary even if the sensor IC is again detached. Alternatively, the practitioner may start the alignment correction process arbitrarily.

Next, the measurement procedure in the bio-information measurement device 10 will describe with reference to FIG. 8. The operator places the measurement device 30 and seeds cells suspended in a culture medium onto the surface of the sensor matrix. As a result, the test samples introduces into the sensor IC (S21). The illumination device 30 is disposed on the top of the measurement device 20 and placed in a state positioned in an incubator as the dark room (not shown). The operator gives an instruction to start the operation from the input unit to the controller 51, and actuates the bio-information measurement device 10 (S22). When operation diagnoses that predetermined conditions of cell information acquisition or conditions of cell information acquisition initiation establishes (S23), the controller 51 controls the censor IC to acquire specific or arbitrary cell information except for optical information by associating the cell information with positional information within the cell matrix. The obtained cell information amplifies in the sensor IC, and sends to the input/output processing circuit 27. The controller 51 sends the electric signal of the cell information to the storage device 53, and stores the signal once therein (S24) ("acquisition and storage of cell information"). The processor 52 performs data analysis on the cell information obtained under the threshold conditions of the program and table predetermined and stored in the storage device 53 (S25). The controller 51 determines whether the result of the analysis of S25 satisfies the predetermined threshold conditions (S26). When the threshold conditions are determined to be satisfied, the processor 52 determines the illumination conditions such as an illumination region, amount of light, wavelength, and incident angle in accordance with the program stored in the storage device 53, the table that maps the threshold conditions with the illumination conditions or the like (S27) ("determination of the illumination conditions"). The illumination conditions decided send to the controller 51. The controller 51 allows the illumination device 30 to control by the control circuit 38 in accordance with the received illumination conditions (S28), and the illumination device 30 performs the light irradiation. Simultaneously with the step, the controller 51 controls a sensor IC matrix 26A and detects the light in the sensor matrix. The detected light information amplifies by the sensor IC matrix 26A, and sends to the input/output processing circuit 27. In the controller 51, an arbitrary conversion performs by the input/output processing circuit 27 and the electric signal of the light information sends to the processor 52. The processor 52 produces an optical image on light information from the light information corresponding to the positional information, and stores the image once in the storage device 53

(S29) ("acquisition and storage of optical image"). The processor 52 determines whether the test sample reaches a predetermined state or satisfies predetermined conditions in accordance with the predetermined conditions or timetable (S31). When the processor 52 determines that the test sample reaches a predetermined state or satisfies predetermined conditions, the process proceeds to S32 and the measurement is terminated (S32). When the processor 52 determines that the test sample does not reach a predetermined state, or does not satisfy predetermined conditions, the process proceeds to S26 and the steps S26 to S30 repeatedly perform in accordance with the predetermined conditions or timetable.

For example, a start of the cell information acquisition in S23 and the determination of the illumination conditions in S26 may control by the controller 51, in accordance with the predetermined conditions or timetable. In the determination of S26, when the result analyzed in S25 does not satisfy the predetermined threshold conditions, the steps of S26 to S30 skip and the steps of S23 to S31 repeat until the threshold conditions are satisfied. In S32, a part or all of the stored information can read out by control of the controller 51 or operator's decision. In such measurement, according to the operator's decision, the entire surface or a part of the sensor matrix irradiates with light at arbitrary timing, and the interrupt control may perform to obtain a two-dimensional image.

Figure 9:
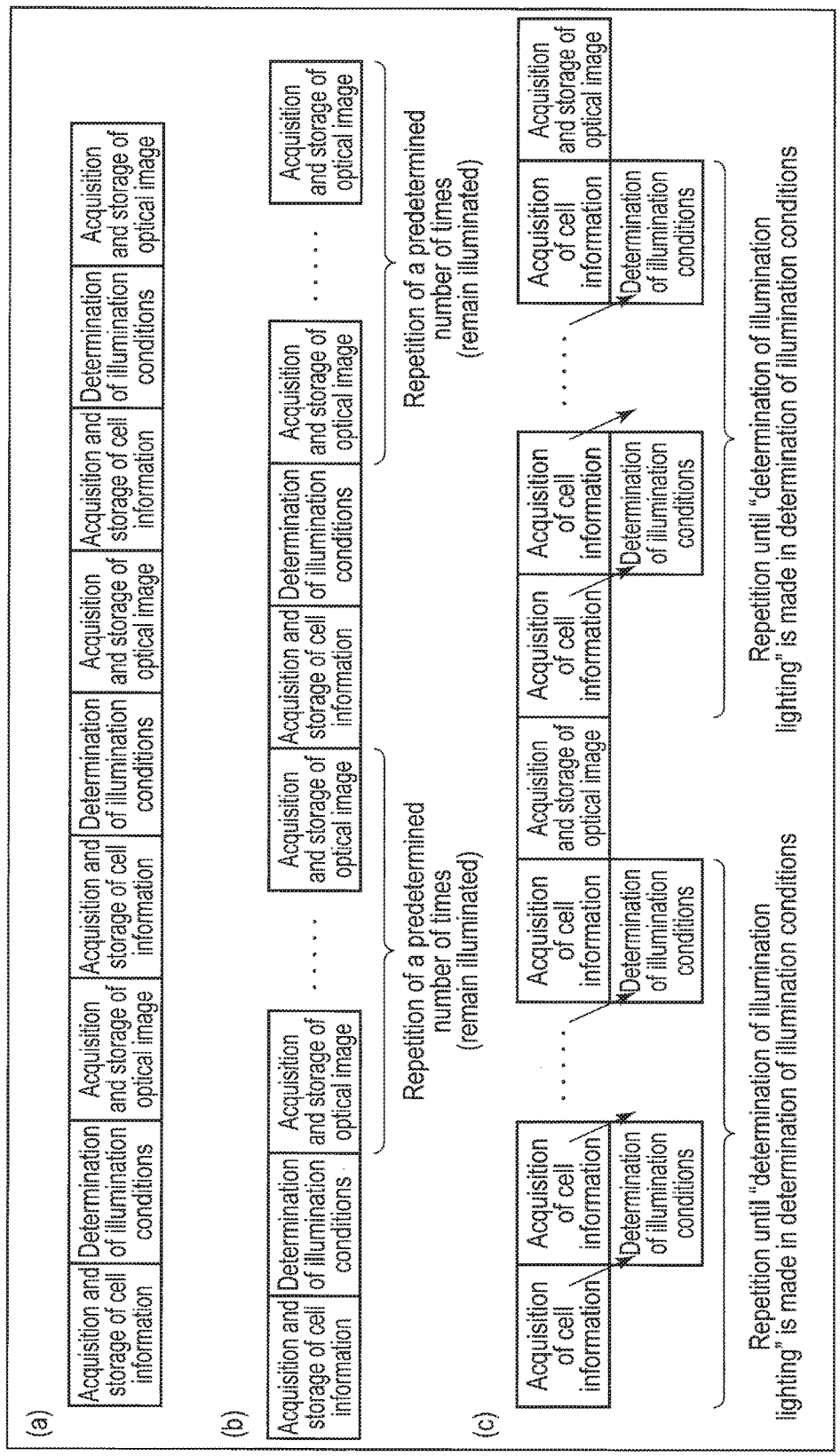
FIG. 9 is a view showing an example of the timing chart used in the measurement by the bio-information measurement device according to the embodiment.

The measurement procedure described using FIG. 8 may executed or change in accordance with the timetables shown in (a) to (c) of FIG. 9. Hereinafter, the operation procedure will further describe based on the timetable.

In the timetable of FIG. 9 (*a*), the bio-information measurement device 10 executes the measurement according to a sequence that repeats a set of "acquisition and storage of cell information", "determination of the illumination conditions", and "acquisition and storage of optical image" at arbitrary frequency. FIG. 9 (*a*) shows an example in which the set repeats three times. However, there is no limitation in the repetition process and it may perform, for example, in accordance with the practitioner's request or information measured. Similarly, the interval between the three steps including in a set and the interval between sets may select, for example, in accordance with the practitioner's request or information measured, the calculation in the processor 52 or both of them.

In the timetable of FIG. 9 (*b*), the bio-information measurement device 10 executes the measurement according to a sequence that repeats a set of "acquisition and storage of cell information", "determination of the illumination conditions", and multiple times of "acquisition and storage of optical image" (i.e., repetition of the step of "acquisition and storage of optical image") at arbitrary frequency. In the case of this sequence, the step of "acquisition and storage of optical image" repeats multiple times as predefined. Similarly to FIG. 9 (*a*), the number of repetitions of the step of "acquisition and storage of optical image" in a set, the interval between the steps in a set, and the interval between sets may select, for example, in accordance with the practitioner's request or information measured, the calculation in the processor 52 or both of them.

In the timetable of FIG. 9 (*c*), the bio-information measurement device 10 repeats the steps of "acquisition and storage of cell information" and "determination of the illumination conditions" until the obtained information satisfies the threshold conditions, and performs the step of "acquisition and storage of optical image" only when the information satisfying the threshold conditions is obtained. These steps define as a set. The bio-information measurement device 10 executes the measurement according to a sequence that repeats the set at arbitrary frequency. Hence, in the steps of "acquisition and storage of cell information" and "determination of the illumination conditions", the light from the illumination device does not emit until "determination of illumination lighting" makes made (the information satisfying the threshold conditions obtained) in the step of determination of the illumination conditions. In this example, the step of "acquisition and storage of cell information" may perform simultaneously with the step of "determination of the illumination conditions". Therefore, it is possible to repeat the two steps many times in a short period time. Similarly to (a) and (b) of FIG. 9, the number of repetitions of the steps of "acquisition and storage of cell information" and "determination of the illumination conditions" in a set, the interval between the steps in a set, and the interval between sets may select, for example, in accordance with the practitioner's request or information measured, the calculation in the processor 52 or both of them.

In any of the three examples, the time required to perform the steps of "acquisition and storage of cell information", "determination of the illumination conditions", and "acquisition and storage of optical image" may select, for example, in accordance with the practitioner's request or information to be measured, the calculation in the processor 52 or both of them.

According to the bio-information measurement device according to such an embodiment, it is possible to obtain information measured. Thus, the test sample can measure more economically, efficiently and accurately. According to an embodiment, a method of sensing of a biological sample using the bio-information measurement device or a method of acquiring cell information using the bio-information measurement device can provide.

Figure 10:
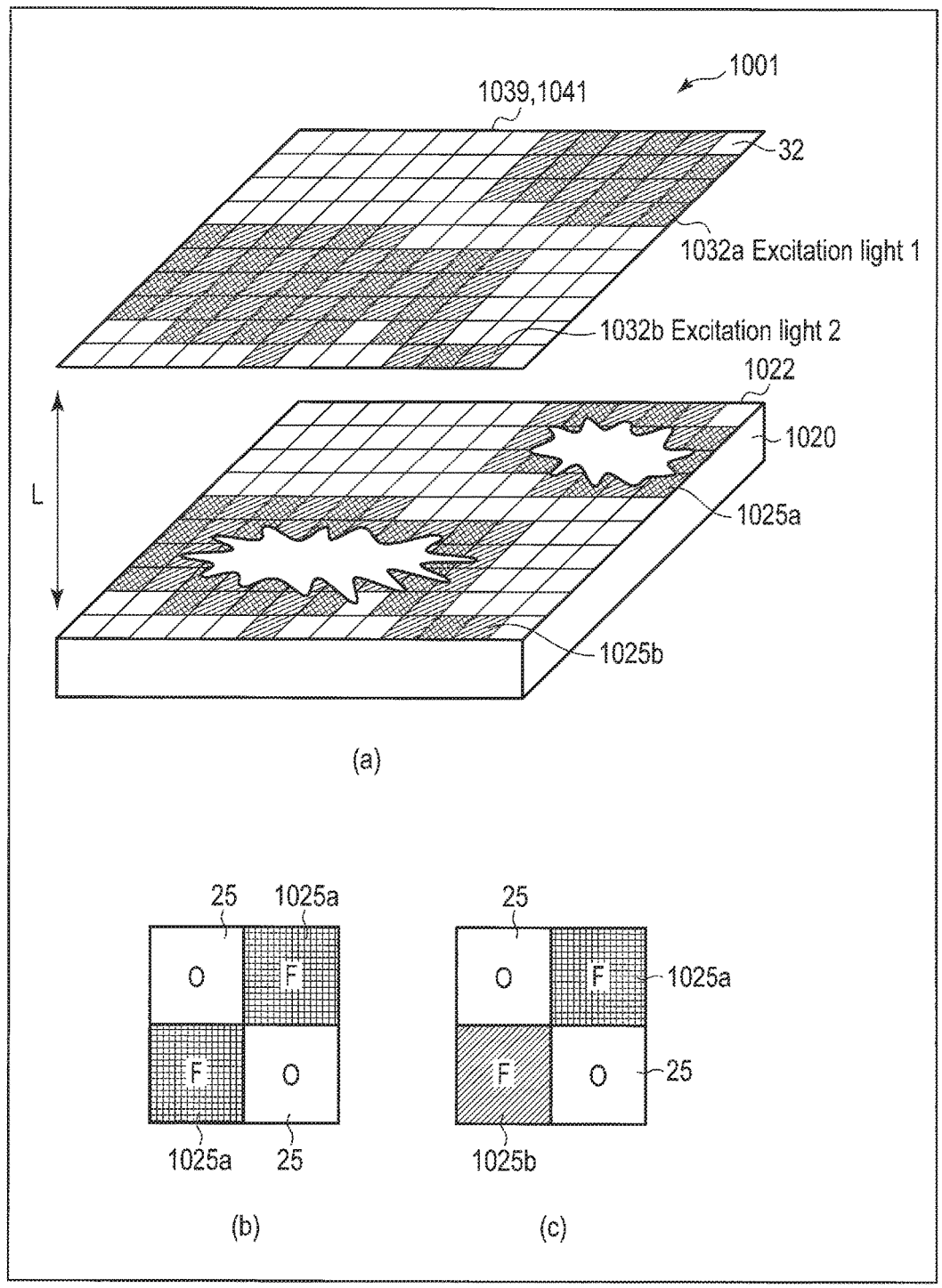
FIG. 10 is an image view showing an example of a sensor matrix or a lighting unit matrix, each matrix being correspondingly included in the bio-information measurement device according to the embodiment.

Examples of the embodiments of the bio-information measurement device will further describe with reference to (a) and (b) of FIG. 10.

A bio-information measurement device 1001 has the same configuration as the bio-information measurement device 10, except for the type and combination of the sensor elements including in the basic blocks and the configuration of the lighting unit. The bio-information measurement device 1001 includes the fluorescence intensity as the light information. A light emitting unit 1039 shown in FIG. 10 (*a*) includes a lighting unit that emits excitation lights having two types of wavelengths and a visible light. Predefined fluorescence light acquires as the light information by irradiating the excitation lights having two types of wavelengths. FIG. 10 (*a*) shows a pattern diagram in which specific regions irradiate with two types of excitation lights in a sensor matrix 1022 disposed a measurement device 1020.

First and second lighting units 1032*a* and 1032*b*, which emit first and second excitation wavelengths, align on a straight line of one direction on a lighting unit matrix 1041 and alternately adjacent to each other.

On the sensor matrix 1022, a first sub sensor pixel 1025*a* emitted a first excitation wavelength into a basic block (as shown in FIG. 10 (*c*)) and sensed a first fluorescence light having a first fluorescence wavelength, a second sub sensor pixel 1025*b* sensed a second fluorescence light having a second fluorescence wavelength, and a third sub sensor pixel 25 sensed information on other types dispose adjacent to different types of pixels in a matrix.

The lighting unit matrix 1041 and the sensor matrix 1022 closely dispose along a line L.

Under the illumination conditions based on the information from the third sub sensor pixel 25, the first excitation wavelength and the second excitation wavelength emit to the sensor matrix 1022. The first sub sensor pixel 1025a and the second sub sensor pixel 1025b wavelength-selectively acquire light information on the test sample.

When the excitation wavelength having a wavelength emits and the fluorescence light having a wavelength is detected, as shown in FIG. 10 (b), sub sensor pixels 1025a for detecting fluorescent information and other types of sub sensor pixels 25 dispose adjacent to different types of pixels.

An excitation light rejection filter may place in each of the sensing units such that a specific single wavelength selectively irradiates.

During detection of fluorescent information, one of the first excitation wavelength and the second excitation wavelength emit and the other turns off. When there is no overlapping between the first excitation wavelength and the first fluorescence wavelength observed corresponding to the first excitation wavelength, and the second excitation wavelength and the second fluorescence wavelength observed corresponding to the second fluorescence wavelength, the first excitation wavelength and the second excitation wavelength may be simultaneously emitted. Even if there is overlapping between the first excitation wavelength and the second excitation wavelength, the first excitation wavelength and the second excitation wavelength may emit simultaneously and the fluorescence wavelengths corresponding thereto may detect, unless these wavelengths interfere with one another on the sensor matrix 1022. The fact that those wavelengths do not interfere with one another may confirm using the bio-information measurement device 10 for which those wavelengths are actually used, or alternatively may be determined by the theory. Further, irradiation with excitation light and fluorescent observation may perform alternately.

Figure 11:
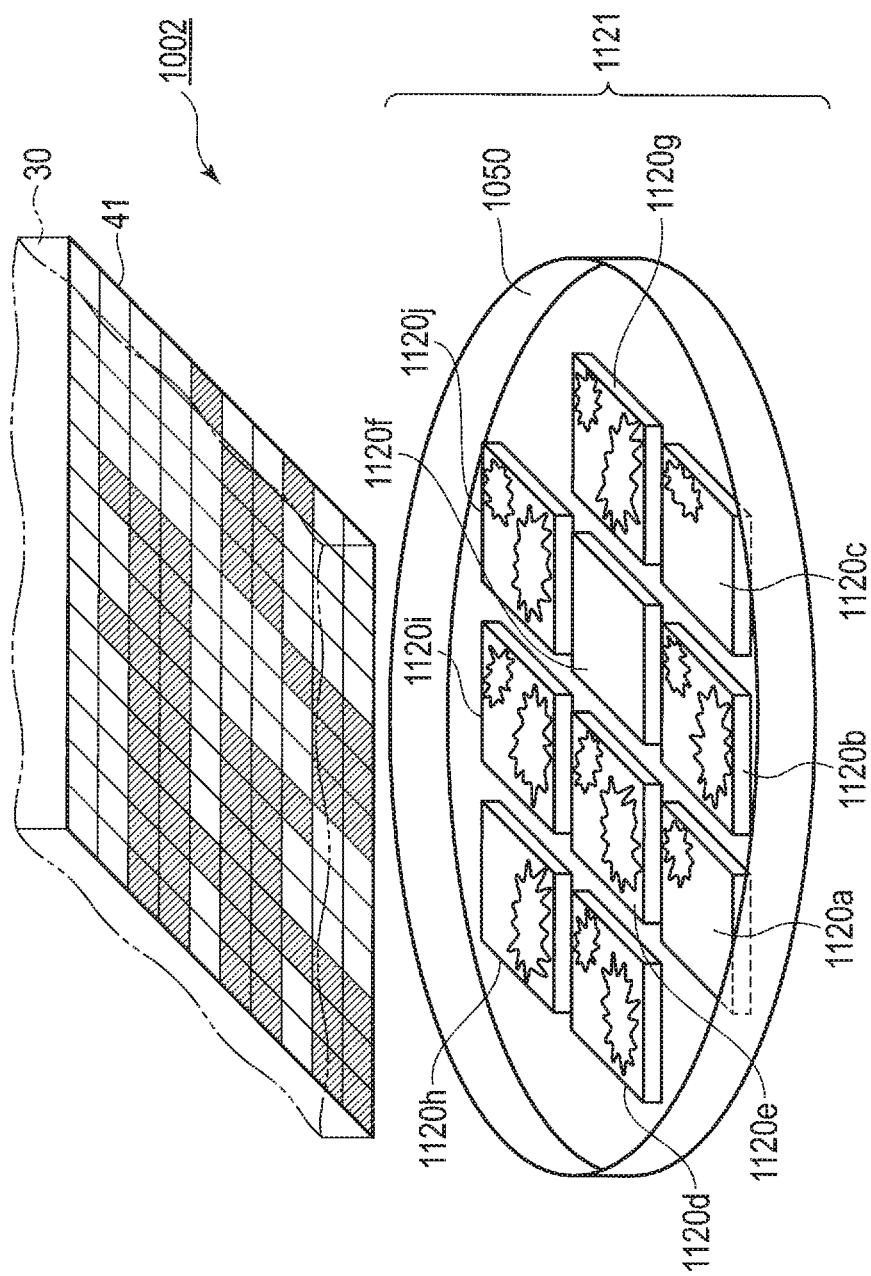
FIG. 11 is an image view showing an example of a sensor matrix or a lighting unit matrix array, which correspondingly includes in the bio-information measurement device according to the embodiment.
Figure 13:
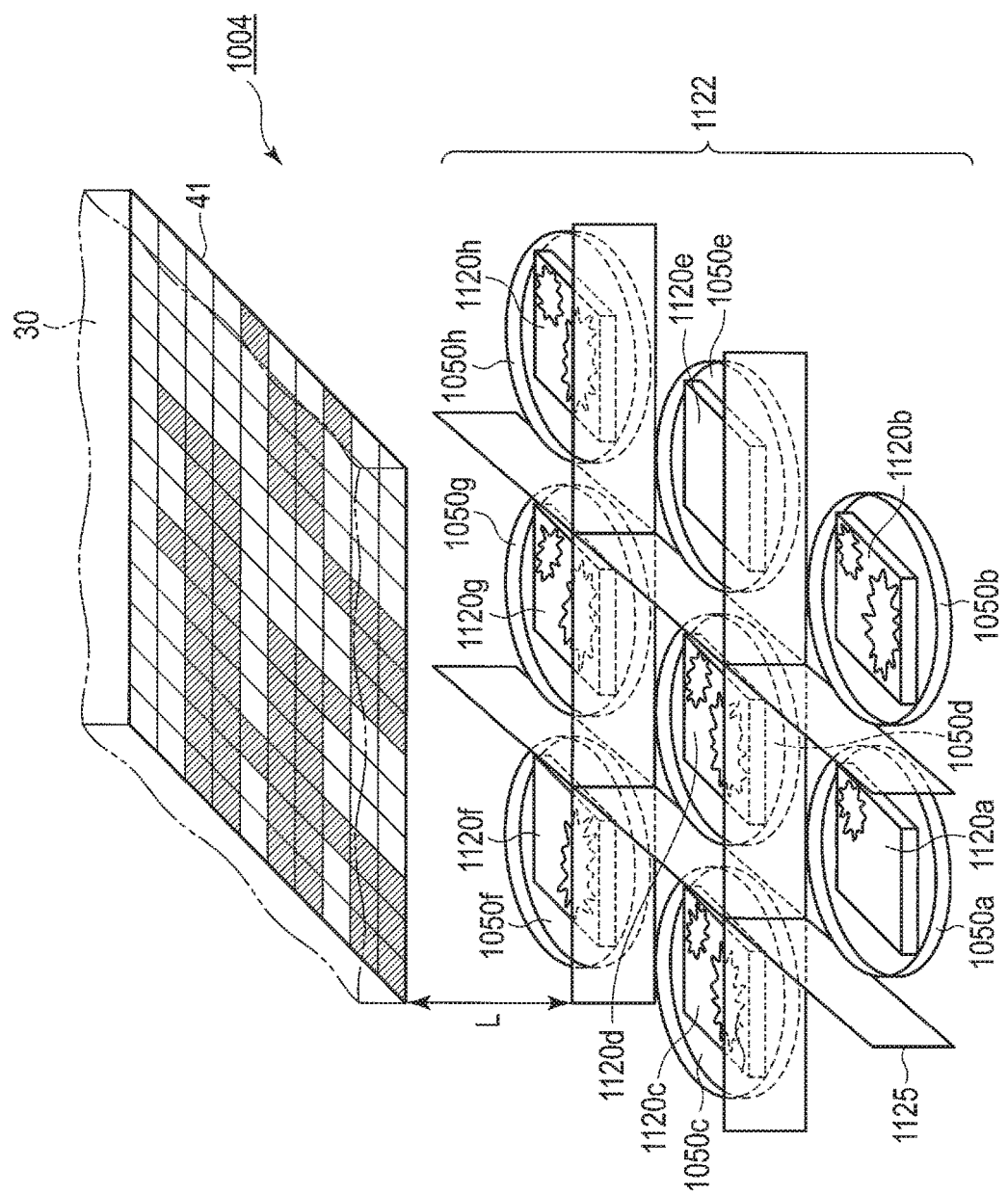
FIG. 13 is an image view showing an example of a sensor matrix or a lighting unit matrix array, which correspondingly includes in the bio-information measurement device according to the embodiment.

Usage examples of the measurement device 20 when an organism or a part thereof uses as the test sample will describe with reference to FIGS. 11 to 13.

Measurement devices 1120a to 1120j (collectively referred to as "measurement device 1120") respectively include sensor matrices. The bio-information measurement device 1002 includes a plurality of the measurement devices 1120 as a measurement device array 1121, in an environment where cells can culture on the sensor matrices. In FIG. 13, such an environment provides by a culture dish 1050 including a culture medium. Thus, the bio-information measurement device 1002 according to an embodiment includes the same configuration as that of the bio-information measurement device 10 except that the measurement device array 1121 is included. Light irradiation to the measurement device array 1121 may perform by the illumination device 30 including a lighting unit matrix having an area covered all the sensor matrices.

The test sample introduces into the bio-information measurement device 1002 in the following manner. First, a plurality of measurement devices 1120a to 1120j, in which the sensor elements select depending on the information detected and the basic blocks design, place in the culture dish 1050 with a suitable size. Then cells suspended in a culture medium seed to the devices (namely, the cell suspension is added). The illumination device 30 attach to the measurement device array 1121 so that the lighting unit matrix faces all the surfaces of the biosensor matrices of the measurement devices 1120, and the positions of the corresponding elements match to each other. Thus, the cells as the test samples introduce into the bio-information measurement device 1002.

The measurement by the bio-information measurement device 1002 may perform in the following manner. First, the bio-information measurement device 1002 places in an incubator in which a suitable environment for cultivation maintains. Then, predefined information on the cells acquires over time while the cells as the test samples cultures for a long period time. The illumination device 30 and the measurement devices 1120 electrically connect to the control unit 40 by radio communication (not shown). The control and operation procedure of the bio-information measurement device 1002 perform as described above.

Configurations of the measurement devices 1120 including in a measurement device array 1121 may be equal to or different from each other, or some of them are equal.

According to the bio-information measurement device 1002, a multi-item test may perform on the cells in a batch under the same conditions. At this time, the selection of illumination conditions, such as an illumination region, determines depending on the presence state of the cells, and thus the process can perform economically or efficiently.

Alternatively, the culture dish 1050 shown in FIG. 11 may prepare in a number equal to the number of the measurement devices 1120 including in the measurement device array 1121 as shown in FIG. 12. Such a bio-information measurement device 1003 includes a plurality of measurement devices 1120 housed in a plurality of culture chambers. Each of the culture chambers may be an independent culture dish or a multi-well chamber having a plurality of culture chambers. The number of wells of the multi-well chamber may select arbitrarily.

On the other hand, the illumination device including in the bio-information measurement device comprising the culture chambers may provide as a lid of a culture vessel, such as a culture dish or a culture chamber. Alternatively, commercially available culture vessels such as a covered culture dish, 6-well, 12-well, 24-well, 48-well, and 96-well multi-well chambers may use for the measurement device array of the bio-information measurement device. In that case, each of the culture dishes or each of the wells may include at least one of the illumination devices. On the other hand, it is possible to produce such a bio-information measurement device by attaching an illumination device to the bottom of the lid of each of the covered culture dish, 6-well, 12-well, 24-well, 48-well, and 96-well multi-well chambers and allowing a lighting unit matrix to face a biosensor matrix. Alternatively, in the case of the bio-information measurement device disposed in an incubator for measurement, a measurement device places on the top surface of the bottom of at least two shelves which are disposed vertically parallel to each other in the incubator and an illumination device attaches to the position corresponding to the lower surface of the top. In that case, the shelves to be disposed may place in the incubator so as to parallel (horizontal) to the mounting surface or the bottom of the incubator.

In the bio-information measurement device including a plurality of culture chambers as described above, a shield member 1125 may provide between the culture chambers as shown in FIG. 13. The illumination device 30 including in a bio-information measurement device 1004 may dispose in contact with the shield member 1125. When the shield member 1125 provides, it is possible to emit light from the illumination device 30 to the measurement device in an independent space. For example, the shield member 1125 may present between adjacent measurement device arrays 1120, or may present between adjacent measurement device array groups (not shown) including the measurement device arrays 1120. In other words, for example, a sensing unit region forms by the presence of the shield member 1125, and a single or plurality of measurement devices (not shown) may present in the sensing unit region. A distance between a lighting unit matrix 41 and a sensor matrix may adjust by allowing the lighting unit matrix 41 to be close to the top of the shield member 1125 along a line L. Alternatively, the top of the shield member 1125 may be in contact with or tightly fixed to the lighting unit matrix 41. The shield member may have a plate shape, a membrane shape or a layer shape. An example of a shading member may be a screen.

Accordingly, since it is possible to provide an independent space to each of the measurement devices including in the bio-information measurement device 1004, it improves design flexibility (e.g., illumination conditions or measurement protocols). Therefore, the target measurement can perform economically or efficiently.

The bio-information measurement device described above is an example in which a measurement device includes a sensor matrix surface and an illumination device includes a lighting unit matrix surface. However, the device is not limited thereto. A measurement device may include a plurality of sensor matrix surfaces and/or an illumination device may include a plurality of lighting unit matrix surfaces. An example of such bio-information measurement device shows in FIG. 14. An illumination device 1139 included in a bio-information measurement device 1005 includes a lighting unit matrix array 1241. The lighting unit matrix array 1241 includes a plurality of lighting unit matrices 1141. The lighting unit matrices 1141 include a plurality of lighting units 32. The bio-information measurement device 1005 includes a sensor matrix array 1122. The sensor matrix array 1122 includes a plurality of sensor matrices 1220a to 1220i. The sensor matrix 1220a includes a plurality of sensor pixels 23. The sensor pixels 23 include a plurality of sub pixels. The sub pixels provide by a sensing unit included in the sensor element (not shown).

In the above example, the environment where the cells as the test samples can culture achieves by placing the measurement device in the culture dish including the culture medium. According to the embodiment, the environment for culturing the cells can achieve without using the culture dish. For example, as shown in FIG. 15, a wall 1322 extending upward from the edge of a substrate 1321 may form so as to surround a sensor matrix 1321 or a sensor matrix array 1321 on a measurement device 1320. The test sample enables to introduce into the bio-information measurement device by adding a cell suspension into the wall 1322.

[Sensor Element]

The sensor element will describe with reference to FIGS. 16 to 19.

Figure 16:
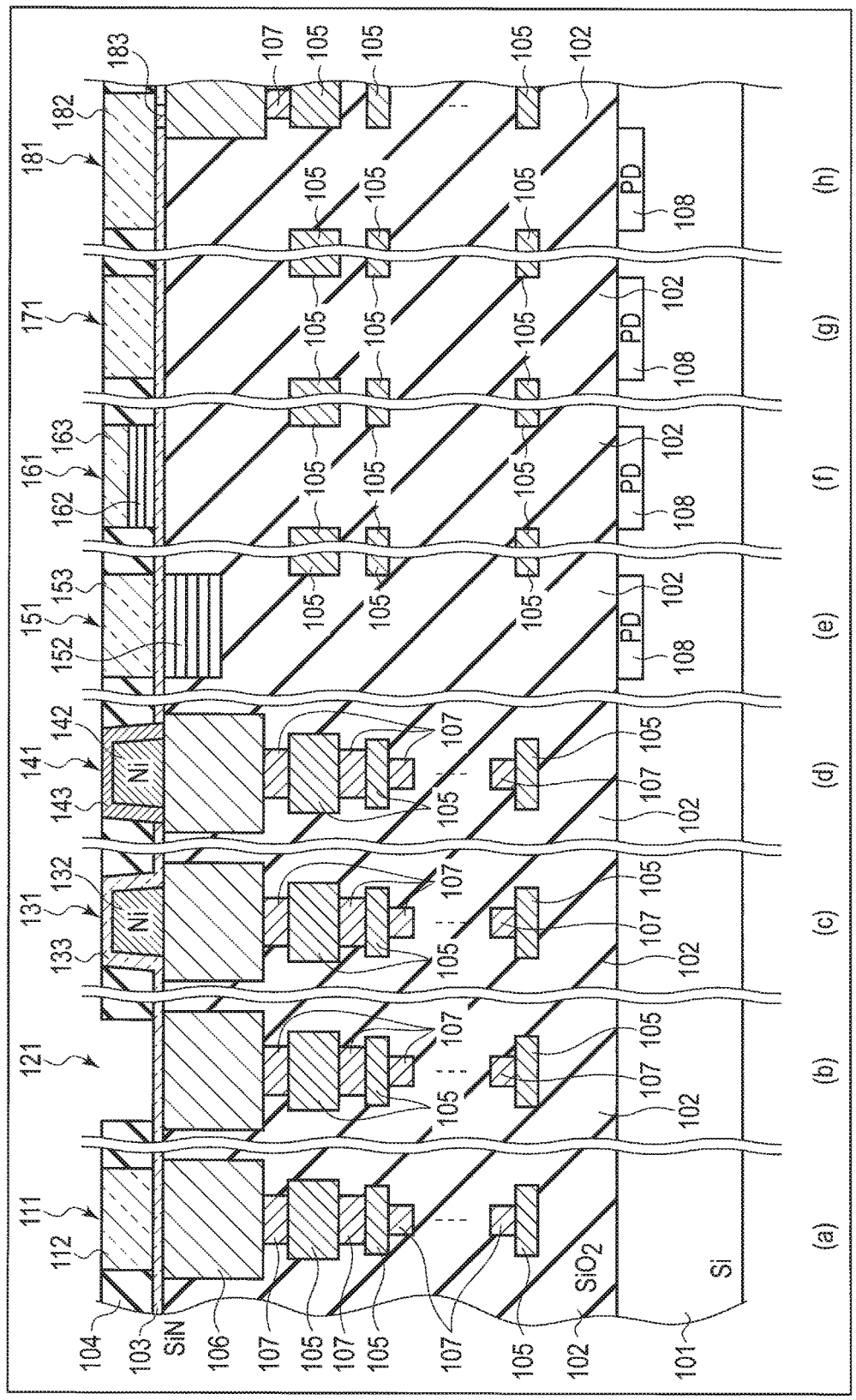
FIG. 16 is a cross-sectional view showing a part of an example of the measurement device according to the embodiment.
Figure 17:
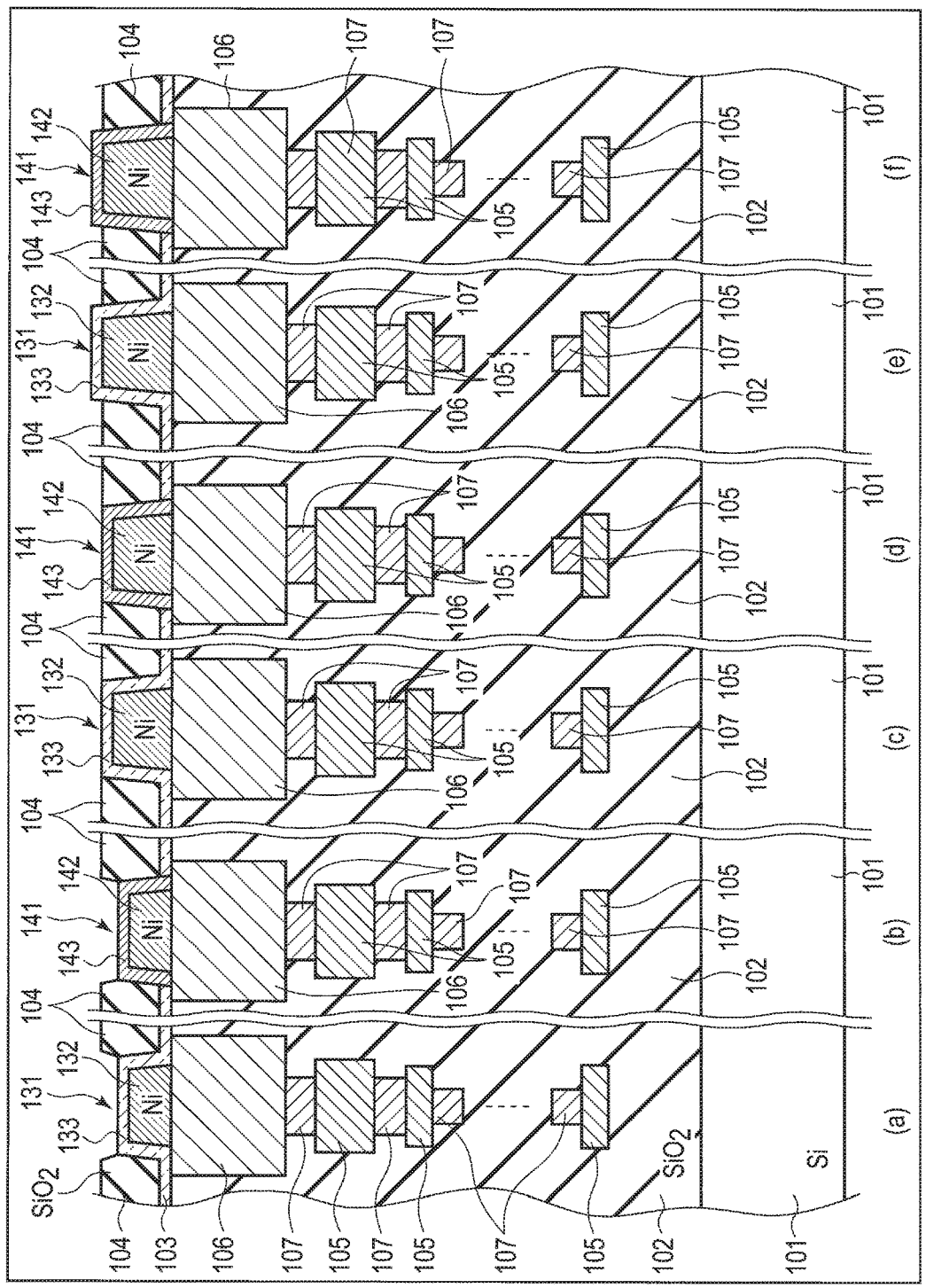
FIG. 17 is a cross-sectional view showing examples of electrode pixels which are included in the measurement device according to the embodiment.

FIGS. 16 and 17 are cross-sectional views of the sensor elements formed on the substrate of the measurement device. The measurement device includes a plurality of pixels (sensor elements) which is divided by a lattice-shaped partition wall 104 formed of an insulating material and/or a metal material and/or a resin on a semiconductor substrate 101. The measurement device includes the silicon substrate 101, a $SiO_2$ layer 102 stacked and formed on the surface of a silicon substrate 101, a silicon nitride layer 103 formed on the surface of the $SiO_2$ layer 102. In the $SiO_2$ layer 102, multilayer wirings 105 form so as to electrically connect to one another by vias 107 formed of a conductor material.

For example, an ion concentration measurement pixel 111, a hydrogen ion concentration measurement pixel 121, a sensor pixel 131 of a first voltage signal, a sensor pixel 141 of a current signal or a second voltage signal, a first photosensor pixel 151, a second photosensor pixel 161, a third photosensor pixel 171, and a fourth photosensor pixel 181 form in the partition wall 104 of FIG. 16, in the order of (a), (b), (c), (d), (e), (f), (g) and (h) in FIG. 16. The wirings form below the pixels to connect to a transistor (not shown). The transistor may form either on the substrate 101 located immediately below the pixel or around the sensing region.

The ion concentration measurement pixel 111 includes an ion sensitive layer 112 formed on the surface of the silicon nitride layer 103. The ion sensitive layer 112 contains, for example, polyvinyl chloride (PVC) as a base substance, and further contains an ionophore such as valinomycin, which selectively binds to a single type of ion, a plasticizer or an exclusion agent. Examples of the ionophore which binds to each ion are as follows: $Na^+$: bis(12-crown-4); $K^+$: bis (benzo-15-crown-5) or valinomycin; $Ca^+$: K23E1; and $NH_4^+$: TD19C6. The ion sensitive layer may form by, for example, an inkjet printing method. The transistor connected to the ion concentration measurement pixel ill detects changes in the ion concentration in the ion sensitive layer 112.

The example in which the ion concentration measurement pixel 111 forms on the surface of the silicon nitride layer 103 describes above. In place of the silicon nitride layer, a silicon oxide layer, an aluminum oxide layer or a tantalum oxide layer may use.

When the ion concentration measurement pixel 111 is formed, it is preferable to previously apply a voltage to the metal (electrode) disposed on the substrate 101 in a position facing an ink jet nozzle (i.e., position corresponding to the ion concentration measurement pixel 111). Thus, it is possible to allow the material (to be inkjet printed) to have directional properties and prevent the material from splattering or splashing.

The hydrogen ion concentration measurement pixel 121 may use the silicon nitride layer 103 as a hydrogen ion sensitive layer. In the hydrogen ion concentration measurement pixel 121, hydrogen ions confirm by detecting the silanol group formed on the surface of the silicon nitride layer 103 as a functional group. The transistor connected to the hydrogen ion concentration measurement pixel 121 detects changes in the ion concentration in the hydrogen ion concentration measurement pixel 121.

Next, an electric sensor pixel will describe with reference to FIGS. 16 and 17. The sensor pixel 131 of a first voltage signal includes, for example, an electrode 132 of metal such as Ni electrically connected to a wiring 106 of an uppermost layer and a silicon nitride layer 133 formed so as to cover the exposed surface of the electrode 132. Preferably, the silicon nitride layer 133 has, for example, a thickness of 20 nm or less. The sensor pixel 131 may produce by forming an electrode of nickel (pedestal) on the surface of the wiring 106 of the uppermost layer and depositing a silicon nitride layer on the exposed surface of the electrode.

The sensor pixel 131 can detect an alternating current voltage signal based on the capacitive coupling between the electrode 132 and the silicon nitride layer 133.

The sensor pixel 141 of a second current signal or a voltage signal includes, for example, an electrode 142 of metal such as Ni electrically connected to a wiring 106 of an uppermost layer and a conductor layer 143 of Pt, Au or Ti, which is formed so as to cover the exposed surface of the electrode 142. The sensor pixel 141 may produce by forming an electrode (pedestal) of platinum, gold or titanium on the surface of the wiring 106 of the uppermost layer and depositing a conductor layer on the exposed surface of the electrode.

The sensor pixel 141 can detect a current signal and an alternating current voltage signal including a low frequency based on the conductance coupling between the electrode 142 and the conductor layer 143.

The first sensor pixel 131 and the second sensor pixel 141 may have any of a recess shape (as shown in FIGS. 16 (*a*) and (*b*)) in which the top surface of the silicon nitride layer 133 or the conductor layer 143 slightly hollows from the top surface of the partition wall 104 as shown in FIG. 17. Also, these pixels 131 and 141 may have any of a flat shape in which the top surface of the silicon nitride layer 133 or the conductor layer 143 is flush with the top surface of the partition wall 104 ((c) and (d) in FIG. 17). Further, these pixels 131 and 141 may have any of a protrusion shape in which the top surface of the silicon nitride layer 133 or the conductor layer 143 slightly protrudes from the top surface of the partition wall 104 (as shown in (e) and (f) of FIG. 16). The transistor connected to the electric sensor pixel may provide in a region except for an IC chip.

The photosensor pixel will describe with reference to FIG. 16. A photodiode (light receiving element) 108 is embedded in each portion of the silicon substrate 101 located immediately below the first to fourth photosensor pixels (151,161,171, and 181) (as shown in (e) to (h) of FIG. 16). The wirings 105 do not present immediately below the first to fourth photosensor pixels (151,161,171, and 181) so that the light from each of the photosensor pixels 151,161, 171, and 181 can receive by the photodiode 108. The light from each of the other photosensor pixels blocks by adjacent wirings so that the light having a predefined wavelength can receive.

The first photosensor pixel 151 includes an inorganic filter 152 formed on the lower surface of the silicon nitride layer 103 and an organic filter 153 formed on the top surface of the silicon nitride layer 103.

The inorganic filter 152 is, for example, a multilayer filter or a plasmon filter. The multilayer filter is a filter obtained by alternately depositing a low refractive material and a high refractive material. For example, when a silicon oxide layer uses as the low refractive material and zirconium dioxide uses as the high refractive material, it is preferable that the silicon oxide layer has a thickness of 62 nm±5 nm and zirconium dioxide has a thickness of 38 nm±5 nm. This multilayer filter can favorably reflect the light having a wavelength of 360 nm±30 nm on the side of a wavelength of 510 nm. Specifically, a rejection ratio of 1/100000 can obtain by stacking a pair of the two oxide layers 30 times. The organic filter 153 may form of a pigment or a dye.

The first photosensor pixel 151 can transmit and absorb a specific wavelength because an optical filter having the inorganic filter 152 and the organic filter 153 include. For example, excitation light removes in the fluorescence measurement and the transmitted fluorescence light detects by the photodiode 108.

The first photosensor pixel 151 applies when the number of layers required for the multilayer filter as the inorganic filter 152 is many. In other words, when the number of layers required for the inorganic filter 152 is many, it is necessary to make the height of the partition wall 104 higher in order to form the inorganic filter on the top surface of the silicon nitride layer 103. This causes a structural defect. In such a case, the inorganic filter 152 forms to be in contact with the lower surface of the silicon nitride layer 103 so that the inorganic filter 152 can form in a necessary number of layers without making the height of the partition wall 104 higher.

The second photosensor pixel 161 includes an inorganic filter 162 that forms on the top surface of the silicon nitride layer 103 and an organic filter 163 that forms on the surface of the inorganic filter 162 to flush with the top surface of the partition wall 104.

The inorganic filter 162 and the organic filter 163 are the same as those used in the first photosensor pixel 151.

The second photosensor pixel 161 can transmit and absorb a specific wavelength, similarly to the first photosensor pixel 151. For example, excitation light removes in the fluorescence measurement and the transmitted fluorescence light detects by the photodiode 108.

The first photosensor pixel 151 applies when the number of layers required for the multilayer filter as the inorganic filter 162 is few. In other words, when the number of layers required for the inorganic filter 162 is few, each of the inorganic filter and the organic filter 163 may form on the top surface of the silicon nitride layer 103.

In the third photosensor pixel 171, no filter is present on the top surface of the silicon nitride layer 103. In the third photosensor pixel 171, an analysis object on the top surface of the silicon nitride layer 103 detects by the visible light from the photodiode 108.

In the third photosensor pixel 171, it permits that a silicon oxide or glass layer forms on the top surface of the silicon nitride layer 103 to flush with the top surface of the partition wall 104 in order to smooth a surface structure, similarly to each of the pixels.

The fourth photosensor pixel 181 includes a transparent electrode 182 that embeds in the partition wall 104 and via fill 183 that connects the wiring 106 located immediately below the partition wall 104 to the transparent electrode 182.

The transparent electrode 182 forms of a conductive oxide such as ITO, InGaZnO or $TiO_2$, or conductive glass.

In the fourth photosensor pixel 181, a voltage applies to the transparent electrode 182 from the wiring 106 through via fill 183. The analysis object on the transparent electrode 182 is migrated, induced or subjected to electrical stimulation. The light emitted in such as state detects by the photodiode 108. Alternatively, an electric signal such as a voltage or potential of the analysis object may measure, simultaneously with the detection of the light by the photodiode 108.

Hereinafter, the method of forming the first photosensor pixel will describe with reference to FIG. 18.

The photodiode 108 forms by doping impurities into the silicon substrate 101. Then, the wirings 105 form while making the $SiO_2$ layer 102 deposited (FIG. 18 (*a*)).

Figure 18:
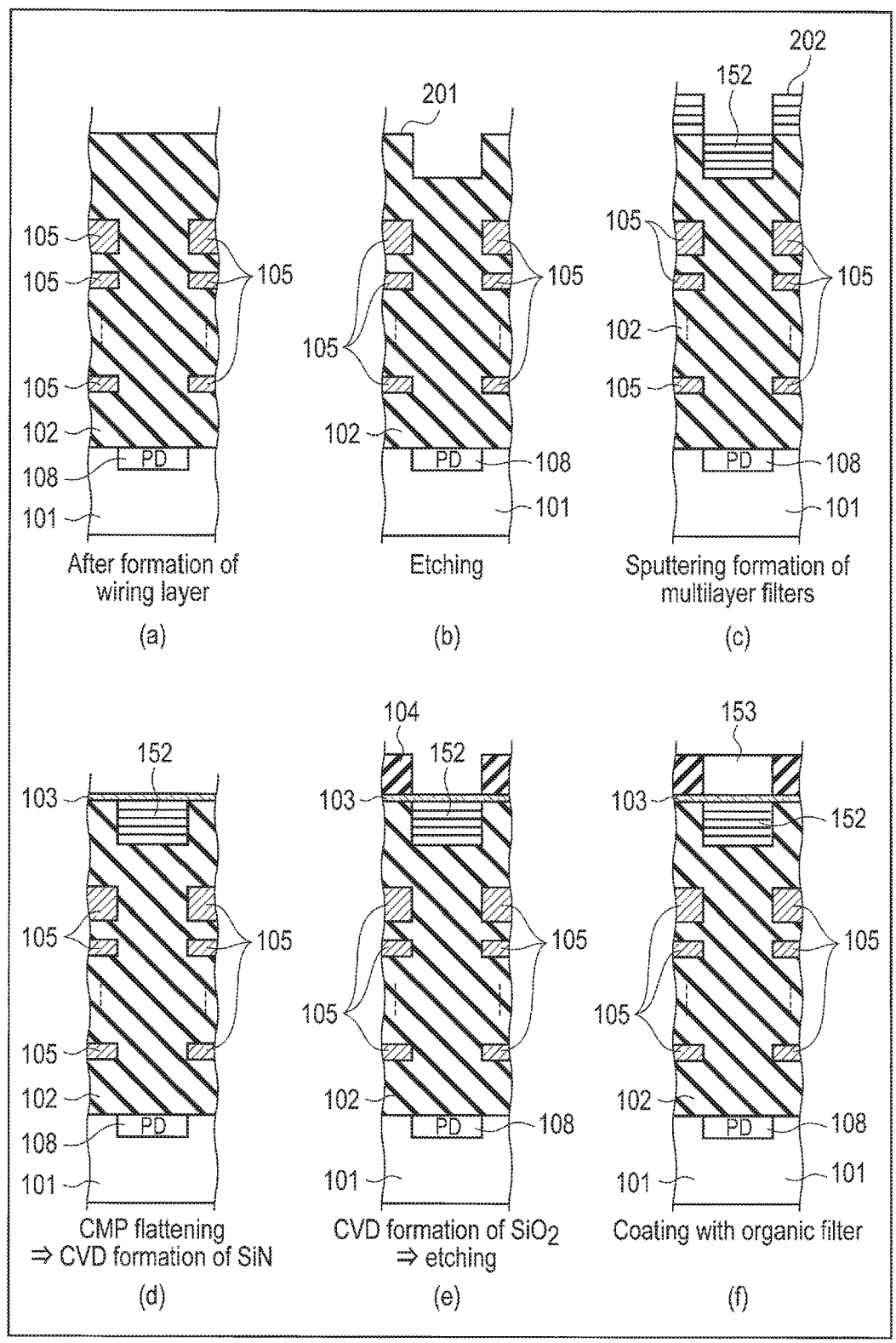
FIG. 18 is a cross-sectional view showing an example of a production process of a photosensor pixel which is included in the measurement device according to the embodiment.

Subsequently, as shown in FIG. 18 (*b*), the surface layer of the $SiO_2$ layer 102 selectively etch to form lattice-shaped protrusions 201. As shown in FIG. 18 (*c*), multilayer layers 202 of an inorganic material form on the surface of the $SiO_2$ layer 102 including the lattice-shaped protrusions 201, for example, by sputtering. Successively, the multilayer filters 202 on the lattice-shaped protrusions 201 selectively polish by chemical mechanical polishing (CMP) and the multilayer filters left between the lattice-shaped protrusions 201. As a result, a plurality of inorganic filters 152 is formed. Thereafter, the silicon nitride layer 103 deposits on the surface of the $SiO_2$ layer 102 including the inorganic filters 152, for example, by a CVD method (FIG. 18 (*d*)).

Then, as shown in FIG. 18 (*e*), partition walls 104 formed of lattice-shaped protrusions of $SiO_2$, similarly to the lattice-shaped protrusions 201, form by depositing a $SiO_2$ layer on the surface of the silicon nitride layer 103, for example, by the CVD method, and then patterning the SiO$_2$ layer. Thereafter, the interior between the partition walls 104 coats with an organic filter material to flush with the surfaces of the partition walls 104 and the interior is dried. The organic filter 153 stacks on the inorganic filters 152 through intermediary of the silicon nitride layer 103. Thus, the first photosensor pixel 151 is formed (FIG. 18 (*f*)). The resulting two filters 152 and 153 are disposed so as to face the photodiode 108.

Here, the organic filter material may apply by the inkjet printing method. At that time, similarly to the formation of the ion concentration measurement FET pixel 111, it is preferable to previously apply a voltage to the metal (electrode) disposed on the substrate 101 in a position facing an ink jet nozzle (i.e., position for forming the organic filter 153). Thus, it is possible to allow the material (to be inkjet printed) to have directional properties and prevent the material from being splattered or splashed.

Hereinafter, the method of forming the second photosensor pixel will describe with reference to FIG. 19.

The photodiode 108 forms by doping impurities into the silicon substrate 101. Then, the wirings 105 form while making the SiO$_2$ layer 102 deposited (FIG. 19 (*a*)).

Figure 19:
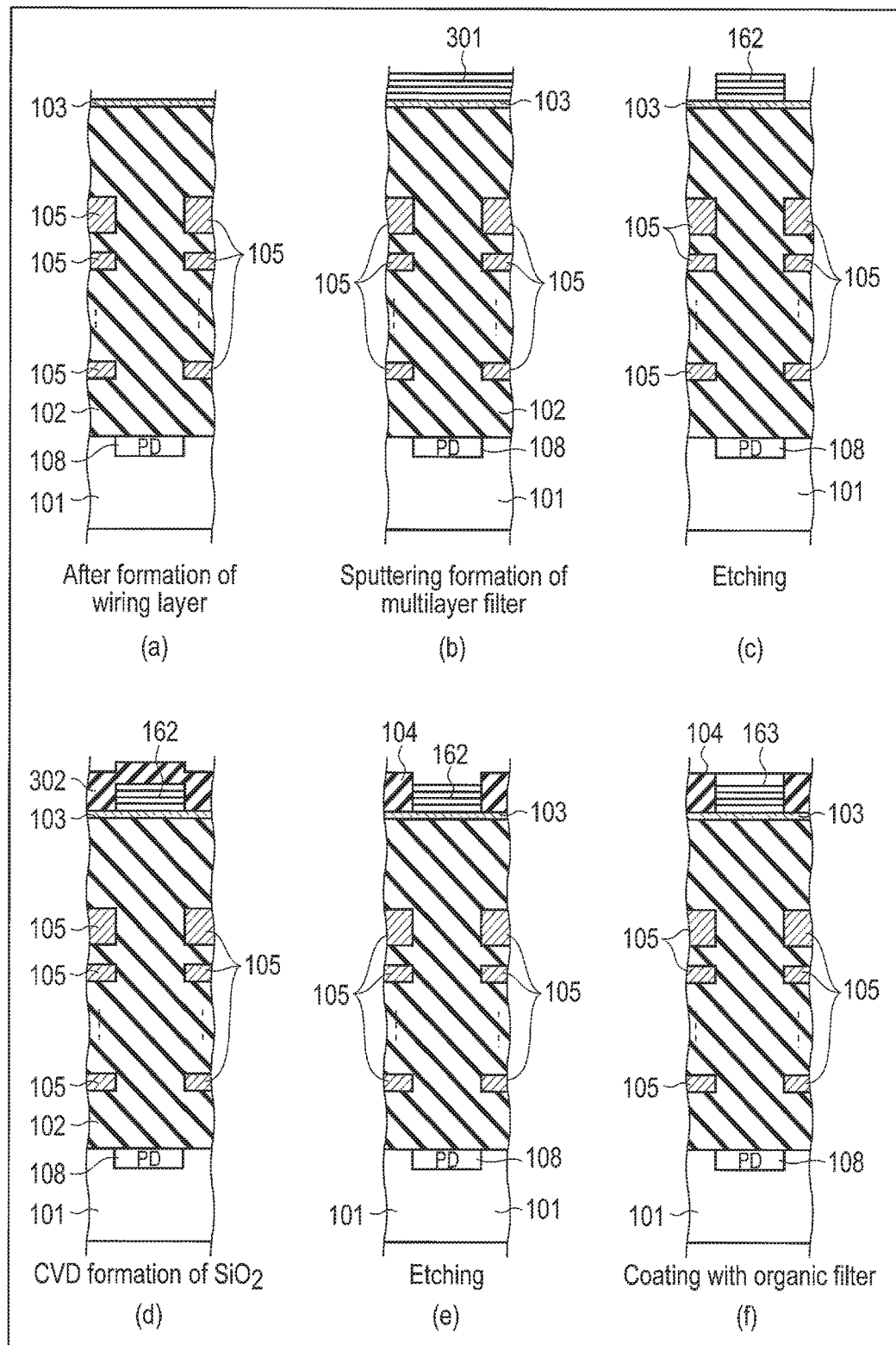
FIG. 19 is a cross-sectional view showing an example of a production process of a photosensor pixel which is included in the measurement device according to the embodiment.

Subsequently, as shown in FIG. 19 (*b*), a multilayer filter 301 of an inorganic material forms on the surface of the silicon nitride layer 103, for example, by sputtering. Successively, the multilayer filter 301 of an inorganic material patterns to form a plurality of the inorganic filters 162 (FIG. 19 (*c*)).

Then, as shown in FIG. 19 (*d*), a SiO$_2$ layer 302 having a thickness larger than that of the inorganic filters 162 forms on the surface of the silicon nitride layer 103 including the inorganic filters 162. Then, as shown in FIG. 19 (*e*), the SiO$_2$ layer 302 on the inorganic filters 162 selectively removes. Lattice-shaped partition walls 104 made of SiO$_2$ and having a thickness larger than that of the inorganic filters 162 form on the surface of the silicon nitride layer 103 so as to surround the inorganic filters 162. Thereafter, the surface of the inorganic filters 162 coats with an organic filter material to flush with the surfaces of the partition walls 104 and the surface is dried. The organic filter 163 stacks on the inorganic filters 162. Thus, the second photosensor pixel 161 is formed (FIG. 19 (*f*)). The resulting two filters 162 and 163 dispose so as to face the photodiode 108.

The material of the wiring 106 may be, for example, copper or aluminum, however it is not limited thereto.

The signals detected by the sensing units of the detection elements send, for example, from a transistor or a light receiving element to a portion of the circuit portion of the measurement device.

A temperature sensor pixel may include, for example, a transistor circuit including a plurality of field effect transistors (FET), which use a phenomenon in which the threshold potential of the field effect transistor (FET) is dependent on temperature. For example, a FET, a diode-connected FET which series-connects to the FET, a series circuit including the FETs, and another FET connect in parallel to one another to form a transistor circuit. It is possible to detect the temperature from the output voltage of the transistor circuit. In such a temperature sensor pixel, the temperature may measure at any of the transistor forming portions of the semiconductor. In that case, the temperature sensor pixel does not need to occupy the region of the surface of the measurement device. Alternatively, a configuration using the FETs may dispose as an independent temperature sensor element.

In any of the sensor elements described above, organic and/or inorganic filters may use in combination with each other. The filter used may be an optical filter such as a pigment or dye filter, or a combination thereof. Further, the frequency of the light passing through the filter may select as predefined. The type, combination, and entire configuration of filter materials may appropriately select depending on a predefined frequency. For example, all the sensor elements including in a measurement device may include any of the filters, or only some sensor elements may include any of the filters. When filters include in a plurality of sensor elements, all the filters may be equal to or different from one another, or some of the filters may be equal to or different from one another.

Next, the circuit configuration of the measurement device will describe with reference to the drawings.

Figure 20:
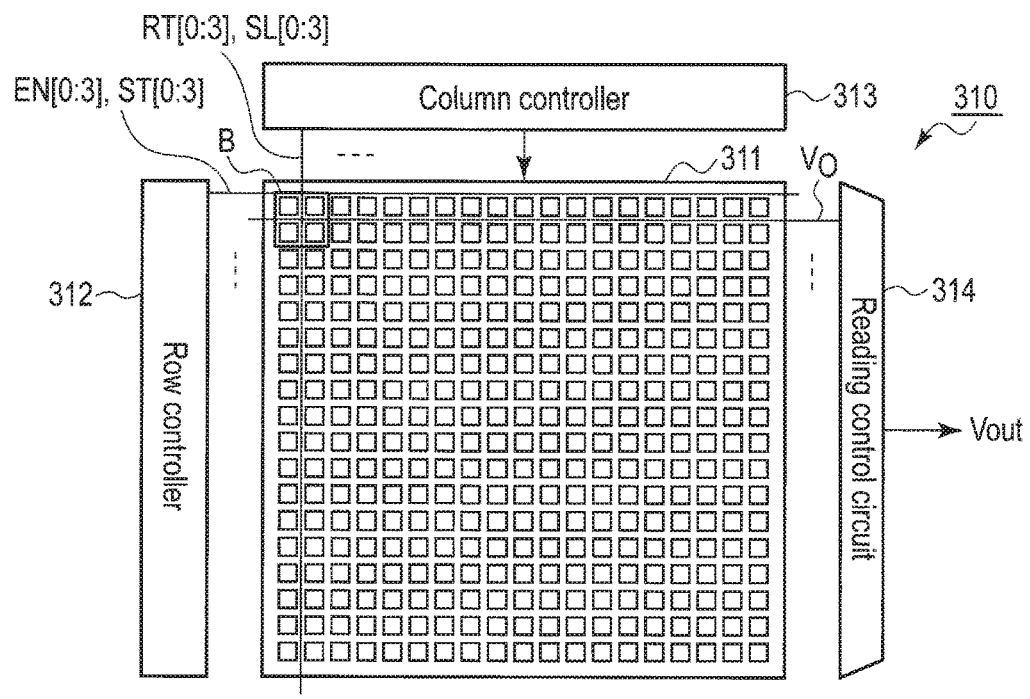
FIG. 20 is a schematic diagram showing an example of a circuit configuration of the measurement device according to the embodiment.
Figure 21:
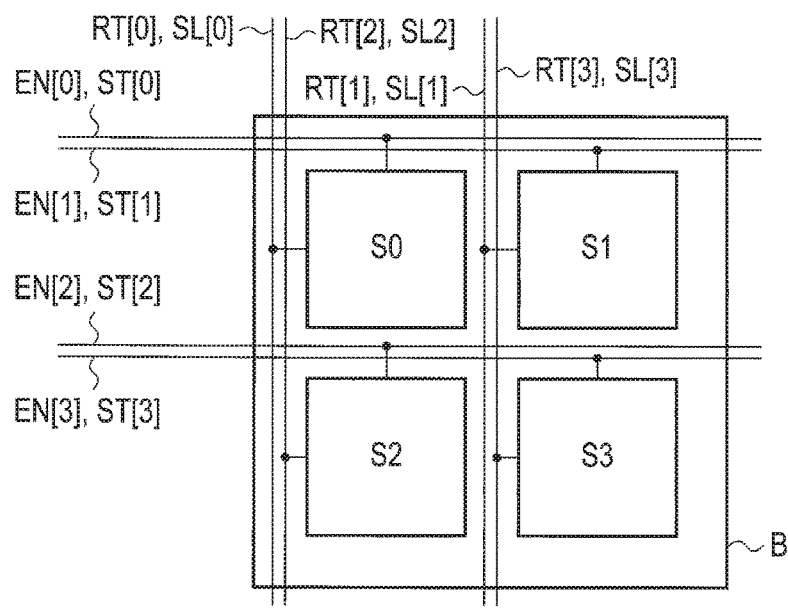
FIG. 21 is a circuit diagram showing an example of each subblock of the measurement device according to the embodiment.

FIG. 20 and FIG. 21 show schematic examples of the circuit configurations of the measurement device according to the embodiment.

A measurement device 310 includes a sensor array 311, a row controller 312, a column controller 313, and an output circuit 314.

The sensor array 311 includes an array of a plurality of basic blocks. The basic blocks include, for example, mutually identical layouts and mutually identical circuit configurations. In this example, a basic block B311 includes subblocks (pixels) S0, S1, S2, and S3. Each of the subblocks S0 to S3 is any one of the ion sensor, electric sensor, and photosensor.

The row controller 312 and the column controller 313 control the operation of detecting data on the pixels disposed in a matrix. For example, the row controller 312 and the column controller 313 control the order of reading out the data from each of the subblocks (sensors).

For example, the row controller 312 generates an enable signal EN and a stimulus signal ST.

The enable signal EN and the stimulus signal ST commonly provide to a plurality of basic blocks arranged in a row direction.

When the signals to be provided to the basic block B are the enable signal EN [0:3] and the stimulus signal ST [0:3], the enable signal EN [0] and the stimulus signal ST [0] provide to a subblock S0, and the enable signal EN [1] and the stimulus signal ST [1] provide to a subblock S1. The enable signal EN [2] and the stimulus signal ST [2] provide to a subblock S2. The enable signal EN [3] and the stimulus signal ST [3] provide to a subblock S3.

The column controller 313 generates a reset signal RT and a transfer signal SL. The reset signal RT is a signal that resets the input voltage of an amplifier for amplifying a detection signal from a sensor. The transfer signal SL is a signal that transmits the output signal of the amplifier to a multiplexer 314.

The reset signal RT and the transfer signal SL commonly provide to a plurality of basic blocks arranged in a column direction.

When the signals to be provided to the basic block B are the reset signal [0:3] and the transfer signal SL [0:3], the reset signal RT [0] and the transfer signal SL [0] provide to the subblock S0, and the reset signal RT [1] and the transfer signal SL [1] provide to the subblock S1. Further, the reset signal RT [2] and the transfer signal SL [2] provide to the subblock S2, and the reset signal RT [3] and the transfer signal SL [3] provide to the subblock S3.

FIG. 21 shows an example of a circuit of subblocks. Each view is an example of a sensor including one of the subblocks (sensors) S0 to S3 of FIG. 20. i represents any one of 0, 1, 2, and 3.

FIG. 21 shows an example when each of the subblocks is an ion sensor or an electric sensor.

Each of the subblocks includes switch elements SW1, SW2, SW3 and SW4. The switch element applies a stimulus voltage Vs to an electrode Ei based on the stimulus signal ST[i]. The switch element SW2 resets an input of an amplifier B to a reset voltage VR based on reset the signal RT[i]. The switch element SW3 transmits the detection signal from the electrode Ei to the amplifier B based on the enable signal EN[i]. The switch element SW4 validates an output signal Vo of the amplifier B based on the transfer signal SL[i].

A P-channel type MOS transistor, an N-channel type MOS transistor or a CMOS switch including both the transistors may use as each of the switch elements SW1, SW2, SW3 and SW4.

Further, a grounded source type amplifier, a grounded drain type amplifier or a differential amplification type amplifier may use as the amplifier B.

FIG. 23 shows an example when each of the subblocks is a photosensor.

Each of the subblocks includes switch elements SW2, SW3 and SW4. The switch element SW2 resets an input of an amplifier B to a reset voltage VR, for example, a power supply voltage Vdd based on the reset signal RT[i]. The switch element SW3 transmits a detection signal from a photodiode (light receiving element) PDi to an amplifier B based on the enable signal EN[i]. The switch element SW4 validates an output signal Vo of the amplifier B based on the transfer signal SL[i].

The order of reading out the data from each of the sensor elements by the circuit may arbitrarily determine as predefined depending on the type of the sensor element included in a biochip. For example, the read-out of a photosensor element, an electric sensor element, and a biochip including a current or a voltage signal sensor element and a temperature sensor element may perform in this order or arbitrary order. The order of read-out and the time may adjust depending on the sensitivity of each of the sensor elements.

The above circuit (as a reading control circuit that controls the read-out of a signal from each sensor element) may connect to each sensor element. A plurality of sensor elements may connect to a circuit. The read-out of a signal may perform by switching of a switch. Further, the reading control circuit may include a controller that controls the order of reading out a signal from a sensor element and an output circuit that outputs the signal from the sensor element to the outside of the circuit under control of the controller.

In addition to the reading control circuit that controls the read-out of a signal from each sensor element, the measurement device may include an A/D conversion circuit as predefined, when A/D conversion is necessary for the signal from the sensor element. Further, in addition to the reading control circuit, the measurement device may include a signal processing circuit that processes a signal from a sensor element in accordance with a previously set procedure. The signal processing circuit also refers to as "a processing circuit" and performs, for example, time integration, auto-zeroing, chopping, correlated double sampling, and/or correlated multiple sampling. The measurement device may further include a communication circuit that transmits the result obtained in the processing circuit to the outside of the circuit, and may furthermore include a memory circuit that stores corresponding of the measurement conditions, measurement procedures, and samples and/or the obtained results and a power circuit that supplies electricity to the measurement device. The circuit including in the measurement device may be any of or a combination of the above circuits.

In the bio-information measurement device according to the embodiment, the test sample measured may be, for example, a biological sample. Examples of the biological sample may include samples derived from animals and plants such as a biological tissue slice, an isolated cell, a cultured cell, a cultured tissue, a cell membrane, an antibody, blood, plasma, serum, urine, stool or mucosa; samples derived from environments such as soil, river, lake, and atmosphere; and microorganisms such as viruses, bacteria and parasites.

The term "isolated cell" means a cell that is collected and isolated from a test sample, i.e., a multicellular organism such as a human or an animal other than a human or a plant, or means an unicellular organism isolated from the environment, such as a microorganism, a fungus, a true fungus, a bacterium or a virus. The term "cultured cell" means a cell obtained by maintaining a cell collected and isolated from any living body or isolated from the environment in a culture medium or a buffer for an arbitrary period time. The term "isolated tissue" means a tissue that is collected and isolated from any living body or a cellular constituent that is present either extracellularly or intracellularly. The isolated tissue may be a slice that obtains by cutting an isolated tissue, if necessary. The term "cultured tissue" means a tissue obtained by maintaining the isolated tissue or its slice in a culture medium or a buffer for an arbitrary period time.

The embodiments may combine with one another, and some of the embodiments may replace with some of the other embodiments.

According to the illumination device and the bio-information measurement device, it is possible to obtain information on a plurality of test items (multi-item) more economically, efficiently and accurately.

In general, measurement devices currently use for examining the limited items in basic research. Further development needs to obtain more information economically, efficiently and accurately.

According to the embodiments, there provides an illumination device for a measurement device capable of obtaining information on a plurality of test items (multi-item) more economically, efficiently and accurately and a bio-information measurement device including the same.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A bio-information measurement device comprising:
a measurement device that includes a substrate and a sensor matrix in a two-dimensional region on the substrate,
wherein the whole sensor matrix forms a sensor pixel array, the sensor matrix includes a plurality of sensor pixels, and each of the sensor pixels consists of a basic block which includes a plurality of sub sensor pixels that are arranged in multiple columns and rows to form a matrix, wherein each of the basic blocks includes at least an optical sensing unit and a pH sensing unit as the sub sensor pixels, and wherein the measurement device obtains (i) optical information and (ii) pH information for a test sample present on the sensor pixel array;

an illumination device that includes a plurality of lighting units disposed to each correspond to a respective one of the basic blocks, wherein the lighting units emit light for each basic block at a light intensity to be emitted toward a region to be irradiated in the sensor pixel array of the measurement device; and a control unit configured to determine the region to be irradiated and vary the light intensity to be emitted to the region to be irradiated for each basic block, based on the pH information obtained by the measurement device, positional information on the sensor pixel array corresponding to the pH information obtained by the measurement device, and predetermined threshold conditions corresponding to the pH information obtained by the measurement device, to control light irradiation of the lighting units in accordance with the determined region and the light intensity for each basic block.

2. The device of claim 1, wherein the lighting units comprise an organic EL display, a liquid crystal display, a laser, a laser array, an LED array, or a laser scanner.

3. The device of claim 1, wherein the plurality of lighting units are configured to emit lights having different wavelengths.

4. The device of claim 3, wherein the lighting units are configured to emit light to the sensor pixel array at different incident angles.

5. The device of claim 3, wherein the illumination device further comprises a wavelength selection filter provided in a light radiation part of each of the lighting units.

6. The device of claim 1, wherein the test sample is a biological sample selected from the group consisting of an isolated cell, a cultured cell, an isolated tissue, and a cultured tissue.

7. The device of claim 6, wherein the optical information comprises information on a cell structure of the biological sample.

8. The device of claim 1, wherein the optical information includes form information on the test sample based on visible light, or intensities of fluorescence, bioluminescence, autofluorescence and/or phosphorescence from the test sample.

9. The device of claim 1, wherein the bio-information measurement device includes a plurality of the measurement devices, and a shield member provided between sensing unit regions each including at least one of the measurement devices.

10. The device of claim 8, wherein the optical information includes a distribution of intensities of fluorescence, bioluminescence, autofluorescence and/or phosphorescence from the test sample.

* * * * *